US008362013B2

(12) United States Patent
Borchardt et al.

(10) Patent No.: US 8,362,013 B2
(45) Date of Patent: Jan. 29, 2013

(54) SALT OF ABT-263 AND SOLID-STATE FORMS THEREOF

(75) Inventors: Thomas Borchardt, Kenosha, WI (US); Paul Brackemeyer, Mt. Prospect, IL (US); Nathaniel Catron, Vernon Hills, IL (US); Rodger Henry, Wildwood, IL (US); Xiaochun Lou, Long Grove, IL (US); Matthew Ravn, Round Lake Beach, IL (US); Geoff G. Z. Zhang, Libertyville, IL (US); Deliang Zhou, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 202 days.

(21) Appl. No.: 12/770,345

(22) Filed: Apr. 29, 2010

(65) Prior Publication Data

US 2010/0305125 A1    Dec. 2, 2010

Related U.S. Application Data

(60) Provisional application No. 61/174,274, filed on Apr. 30, 2009.

(51) Int. Cl.
*A61K 31/535* (2006.01)
*C07D 413/12* (2006.01)

(52) U.S. Cl. .................................... 514/235.8; 544/121
(58) Field of Classification Search .................. 544/121; 514/235.8
See application file for complete search history.

(56) References Cited

U.S. PATENT DOCUMENTS

| | | | |
|---|---|---|---|
| 5,536,729 A | 7/1996 | Waranis et al. | |
| 5,538,737 A | 7/1996 | Leonard et al. | |
| 5,559,121 A | 9/1996 | Harrison et al. | |
| 5,635,187 A | 6/1997 | Bathurst et al. | |
| 5,645,856 A | 7/1997 | Lacy et al. | |
| 5,665,379 A | 9/1997 | Herslof et al. | |
| 6,267,985 B1 | 7/2001 | Chen et al. | |
| 6,309,663 B1 | 10/2001 | Patel et al. | |
| 6,451,339 B2 | 9/2002 | Patel et al. | |
| 6,464,987 B1 | 10/2002 | Fanara et al. | |
| 6,964,946 B1 | 11/2005 | Gutierrez-Rocca et al. | |
| 7,390,799 B2 | 6/2008 | Bruncko et al. | |
| 7,973,161 B2 | 7/2011 | Bruncko et al. | |
| 2007/0027135 A1 | 2/2007 | Bruncko et al. | |
| 2007/0072860 A1 | 3/2007 | Bruncko et al. | |
| 2007/0104780 A1* | 5/2007 | Lipari et al. .................. | 424/456 |
| 2009/0149461 A1 | 6/2009 | Krivoshik | |
| 2010/0278905 A1 | 11/2010 | Catron et al. | |
| 2010/0278921 A1 | 11/2010 | Fischer et al. | |
| 2010/0297194 A1 | 11/2010 | Catron et al. | |
| 2010/0305125 A1 | 12/2010 | Borchardt et al. | |
| 2010/0323020 A1 | 12/2010 | Gokhale et al. | |
| 2011/0071151 A1 | 3/2011 | Zhang et al. | |

FOREIGN PATENT DOCUMENTS

| | | |
|---|---|---|
| CN | 101220008 A | 7/2008 |
| CN | 101798292 A | 8/2010 |
| WO | 2009073835 A1 | 6/2009 |
| WO | 2009155386 A1 | 12/2009 |
| WO | 2011034934 A1 | 3/2011 |

OTHER PUBLICATIONS

Berge et al., Journal of Pharmaceutical Sciences, vol. 66, No. 1, Jan. 1977, pp. 1-19.*
Lessene et al., Dec. 2008, Nature Reviews Drug Dsicovery, vol. 7, pp. 989-1000.*
Caira M.R., "Crystalline Polymorphism of Organic Compounds," Topics in Current Chemistry, 1998, vol. 198, pp. 163-208.
Gould., "Salt Selection for Basic Drugs," International Journal of Pharmaceutics, 1986, vol. 33, pp. 201-217.
International Search Report for Application No. PCT/US2010/033072, mailed on Jul. 12, 2010, 4 pages.
Bruncko M., et al, "Studies leading to potent, dual inhibitors of Bcl-2 and Bcl-xL" Journal of Medicinal Chemistry, 2007, 50 (4), 641-662.
Hanahan D., et al., "The Hallmarks of Cancer", Cell, 2000;100: pp. 57-70.
Hovorka S.W., et al., "Oxidative degradation of pharmaceuticals: Theory, mechanisms and inhibition", Journal of Pharmaceutical Sciences, 2001; 90 (3): 253-269.
Kibbe A.H., ed., Handbook of Pharmaceutical Excipients, 3rd edition. American Pharmaceutical Association, 2000, Table of Contents.
Sutton V.R., et al. "Bcl-2 prevents apoptosis induced by perforin and granzyme B, but not that mediated by whole cytotoxic lymphocytes", Journal of Immunology, 1997, 158 (12), pp. 5783-5790.
Tse et al., "ABT-263: A Potent and Orally Bioavailable Bcl-2 Family Inhibitor," Cancer Research , 2008, 68 (9), pp. 3421-3428.
Chawla, Garima et al., Polymorphism of pharmaceuticals: Challenges and opportunities, Article, Oct. 23, 2003, 3 pages, www.expresspharmaonline.com/20031023/edit02.shtml.
Park, Cheol-Min et al., Discovery of an Orally Bioavailable Small Molecule nhibitor of Prosurvival B-Cell Lymphoma 2 Proteins, J. Med. Chem., 2008, pp. 6902-6915, vol. 51, No. 21.
Wang, Guangjun, et al., An Efficient Synthesis of ABT-263, a Novel Inhibitor of Antiapoptotic Bcl-2 Proteins, Synthesis, Feb. 27, 2008, pp. 2398-2404 No. 15.
Trotta et al., European Journal of Pharmaceutics and Biopharmaceutics 53 (2002) 203-208.
Anonymous: "Phosal(TM) 53 MCT"[Online] Feb. 2007, XP002601344 Phospholipid GmbH—American Lecithin Retrieved from the Internet: URL:http://www.americanlecithin.com/TDS/TDS53MCT.PDF.

* cited by examiner

*Primary Examiner* — Rebecca Anderson

(57) ABSTRACT

ABT-263 bis-HCl and crystalline polymorphs thereof are suitable active pharmaceutical ingredients for pharmaceutical compositions useful in treatment of a disease characterized by overexpression of one or more anti-apoptotic Bcl-2 family proteins, for example cancer.

10 Claims, 2 Drawing Sheets

SALT OF ABT-263 AND SOLID-STATE FORMS THEREOF

CROSS-REFERENCE TO RELATED APPLICATIONS

This application claims priority benefit of U.S. Provisional Application Ser. No. 61/174,274 filed on Apr. 30, 2009.

Cross-reference is made to the following co-filed U.S. applications containing subject matter related to the present application: Ser. No. 12/770,122, titled "Lipid formulation of apoptosis promoter", which claims priority benefit of U.S. provisional application Ser. No. 61/174,245 filed on Apr. 30, 2009; Ser. No. 12/770,174, titled "Stabilized lipid formulation of apoptosis promoter", which claims priority benefit of U.S. provisional application Ser. No. 61/174,299 filed on Apr. 30, 2009 and Ser. No. 61/289,254 filed on Dec. 22, 2009; Ser. No. 12/770,205, titled "Solid oral formulation of ABT-263", which claims priority benefit of U.S. provisional application Ser. No. 61/174,318 filed on Apr. 30, 2009; and Ser. No. 12/770,299, titled "Formulation for oral administration of apoptosis promoter", which claims priority benefit of above-referenced U.S. provisional application Ser. No. 61/174,274, Ser. No. 61/174,299, Ser. No. 61/174,318 and Ser. No. 61/289,254, as well as Ser. No. 61/185,105 filed on Jun. 8, 2009, Ser. No. 61/185,130 filed on Jun. 8, 2009, Ser. No. 61/218,281 filed on Jun. 18, 2009, and Ser. No. 61/289,289 filed on Dec. 22, 2009.

The entire disclosure of each of the above applications is incorporated herein by reference.

FIELD OF THE INVENTION

The present invention relates to the apoptosis-promoting agent ABT-263, and to methods of use thereof for treating diseases characterized by overexpression of anti-apoptotic Bcl-2 family proteins. More particularly the invention relates to a novel salt of ABT-263 and solid-state forms thereof useful, for example, as active pharmaceutical ingredient (API) in preparing pharmaceutical compositions for administration of ABT-263 to a subject in need thereof.

BACKGROUND OF THE INVENTION

Evasion of apoptosis is a hallmark of cancer (Hanahan & Weinberg (2000) *Cell* 100:57-70). Cancer cells must overcome a continual bombardment by cellular stresses such as DNA damage, oncogene activation, aberrant cell cycle progression and harsh microenvironments that would cause normal cells to undergo apoptosis. One of the primary means by which cancer cells evade apoptosis is by up-regulation of anti-apoptotic proteins of the Bcl-2 family.

Compounds that occupy the BH3 binding groove of Bcl-2 proteins have been described, for example by Bruncko et al. (2007) *J. Med. Chem.* 50:641-662. These compounds have included N-(4-(4-((4'-chloro-(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzene-sulfonamide, otherwise known as ABT-737, which has the formula:

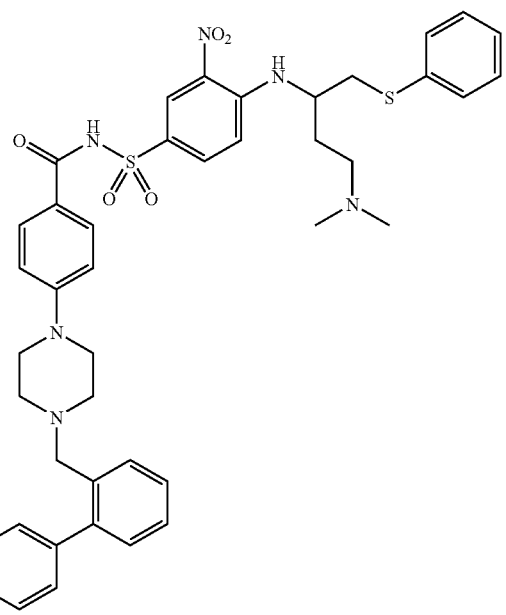

ABT-737 binds with high affinity (<1 nM) to proteins of the Bcl-2 family (specifically Bcl-2, Bcl-$X_L$ and Bcl-w). It exhibits single-agent activity against small-cell lung cancer (SCLC) and lymphoid malignancies, and potentiates pro-apoptotic effects of other chemotherapeutic agents. ABT-737 and related compounds, and methods to make such compounds, are disclosed in U.S. Patent Application Publication No. 2007/0072860 of Bruncko et al.

More recently, a further series of compounds has been identified having high binding affinity to Bcl-2 family proteins. These compounds, and methods to make them, are disclosed in U.S. Patent Application Publication No. 2007/0027135 of Bruncko et al. (herein "the '135 publication"), incorporated by reference herein in its entirety, and can be seen from their formula to be structurally related to ABT-737.

One compound, identified as "Example 1" in the '135 publication, is N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino-3-((trifluoromethyl)sulfonyl) benzenesulfonamide, otherwise known as ABT-263. This compound has a molecular weight of 974.6 g/mol and has the formula:

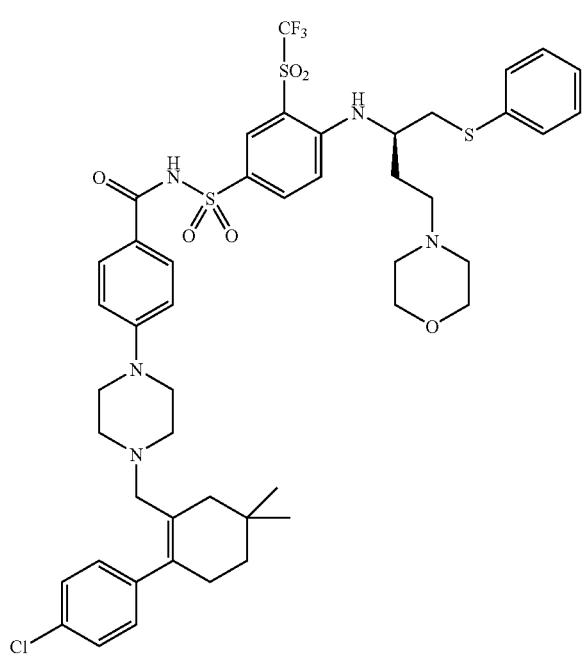 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1]

The '135 publication indicates that certain compounds disclosed therein may exist as acid addition salts, basic addition salts or zwitterions. Acid addition salts of such compounds are said to include acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate and undecanoate salts.

A particular type of disease for which improved therapies are needed is non-Hodgkin's lymphoma (NHL). NHL is the sixth most prevalent type of new cancer in the U.S. and occurs primarily in patients 60-70 years of age. NHL is not a single disease but a family of related diseases, which are classified on the basis of several characteristics including clinical attributes and histology.

One method of classification places different histological subtypes into two major categories based on natural history of the disease, i.e., whether the disease is indolent or aggressive. In general, indolent subtypes grow slowly and are generally incurable, whereas aggressive subtypes grow rapidly and are potentially curable. Follicular lymphomas are the most common indolent subtype, and diffuse large-cell lymphomas constitute the most common aggressive subtype. The oncoprotein Bcl-2 was originally described in non-Hodgkin's B-cell lymphoma.

Treatment of follicular lymphoma typically consists of biologically-based or combination chemotherapy. Combination therapy with rituximab, cyclophosphamide, doxorubicin, vincristine and prednisone (R-CHOP) is routinely used, as is combination therapy with rituximab, cyclophosphamide, vincristine and prednisone (RCVP). Single-agent therapy with rituximab (targeting CD20, a phosphoprotein uniformly expressed on the surface of B-cells) or fludarabine is also used. Addition of rituximab to chemotherapy regimens can provide improved response rate and increased progression-free survival.

Radioimmunotherapy agents, high-dose chemotherapy and stem cell transplants can be used to treat refractory or relapsed non-Hodgkin's lymphoma. Currently, there is not an approved treatment regimen that produces a cure, and current guidelines recommend that patients be treated in the context of a clinical trial, even in a first-line setting.

First-line treatment of patients with aggressive large B-cell lymphoma typically consists of rituximab, cyclophosphamide, doxorubicin, vincristine and prednisone (R-CHOP), or dose-adjusted etoposide, prednisone, vincristine, cyclophosphamide, doxorubicin and rituximab (DA-EPOCH-R).

Most lymphomas respond initially to any one of these therapies, but tumors typically recur and eventually become refractory. As the number of regimens patients receive increases, the more chemotherapy-resistant the disease becomes. Average response to first-line therapy is approximately 75%, 60% to second-line, 50% to third-line, and about 35-40% to fourth-line therapy. Response rates approaching 20% with a single agent in a multiple relapsed setting are considered positive and warrant further study.

Current chemotherapeutic agents elicit their antitumor response by inducing apoptosis through a variety of mechanisms. However, many tumors ultimately become resistant to these agents. Bcl-2 and Bcl-$X_L$ have been shown to confer chemotherapy resistance in short-term survival assays in vitro and, more recently, in vivo. This suggests that if improved therapies aimed at suppressing the function of Bcl-2 and Bcl-$X_L$ can be developed, such chemotherapy-resistance could be successfully overcome.

SUMMARY OF THE INVENTION

The compound ABT-263, when prepared according to Example 1 of the '135 publication, is recovered as an amorphous, glassy solid that is not well suited as active pharmaceutical ingredient (API) for downstream formulation. The present inventors have now prepared a novel bis-acid addition salt of ABT-263 in a number of solid crystalline forms suitable for use as API in a wide variety of formulation types, including those where the API is present in particulate form together with excipients, for example in orally deliverable tablets or capsules. Furthermore, it has been discovered that pharmaceutical compositions comprising the novel salt exhibit oral bioavailability that is at least comparable to, and in some cases superior to, that of a 2 mg/ml solution of ABT-263 free base in a carrier consisting of PEG-400 and DMSO in a 9:1 weight ratio, reported in the '135 publication.

In one embodiment, the invention provides N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino-3-((trifluoromethyl)sulfonyl)benzenesulfonamide bis-hydrochloride (ABT-263 bis-HCl).

In a further embodiment, the invention provides crystalline Form I ABT-263 bis-HCl as characterized herein.

In a still further embodiment, the invention provides crystalline Form II ABT-263 bis-HCl as characterized herein.

In a still further embodiment, the invention provides a variety of solvated crystal forms of ABT-263 bis-HCl, including ethanol, 1-propanol, 2-propanol, 2-butanol, t-butanol, nitromethane, acetonitrile, propionitrile, ethyl formate, methyl acetate, ethyl acetate, isopropyl acetate, acetone, 2-butanone (methyl ethyl ketone, MEK), methyl isopropyl ketone, 1,4-dioxane, benzene, toluene and butyl ether solvates.

In a still further embodiment, the invention provides a process for preparing Form I ABT-263 bis-HCl, comprising desolvating an ethanol, 1-propanol, 2-propanol, 2-butanol, t-butanol, acetonitrile, propionitrile, ethyl formate, methyl acetate, ethyl acetate, isopropyl acetate, acetone, methyl isopropyl ketone, 1,4-dioxane, benzene, toluene or butyl ether solvate form of ABT-263 bis-HCl.

In a still further embodiment, the invention provides a process for preparing Form II ABT-263 bis-HCl, comprising desolvating a MEK solvate form of ABT-263 bis-HCl.

In a still further embodiment, the invention provides a pharmaceutical composition comprising ABT-263 bis-HCl and one or more pharmaceutically acceptable excipients.

In a still further embodiment, the invention provides a method for treating a disease characterized by apoptotic dysfunction and/or overexpression of an anti-apoptotic Bcl-2 family protein, comprising administering to a subject having the disease a therapeutically effective amount of ABT-263 bis-HCl or a pharmaceutical composition comprising ABT-263 bis-HCl and one or more pharmaceutically acceptable excipients. Examples of such a disease include many neoplastic diseases including cancers. A specific illustrative type of cancer that can be treated according to the present method is non-Hodgkin's lymphoma. Another specific illustrative type of cancer that can be treated according to the present method is chronic lymphocytic leukemia. Yet another specific illustrative type of cancer that can be treated according to the present method is acute lymphocytic leukemia, for example in a pediatric patient.

There is still further provided a method for maintaining in bloodstream of a human cancer patient, for example a patient having non-Hodgkin's lymphoma, chronic lymphocytic leukemia or acute lymphocytic leukemia, a therapeutically effective plasma concentration of ABT-263 and/or one or more metabolites thereof, comprising administering to the subject a pharmaceutical composition comprising ABT-263 bis-HCl and one or more pharmaceutically acceptable excipients, in a dosage amount equivalent to about 50 to about 500 mg ABT-263 per day, at an average dosage interval of about 3 hours to about 7 days.

Additional embodiments of the invention, including more particular aspects of those provided above, will be found in, or will be evident from, the detailed description that follows.

DETAILED DESCRIPTION

Figure 1:
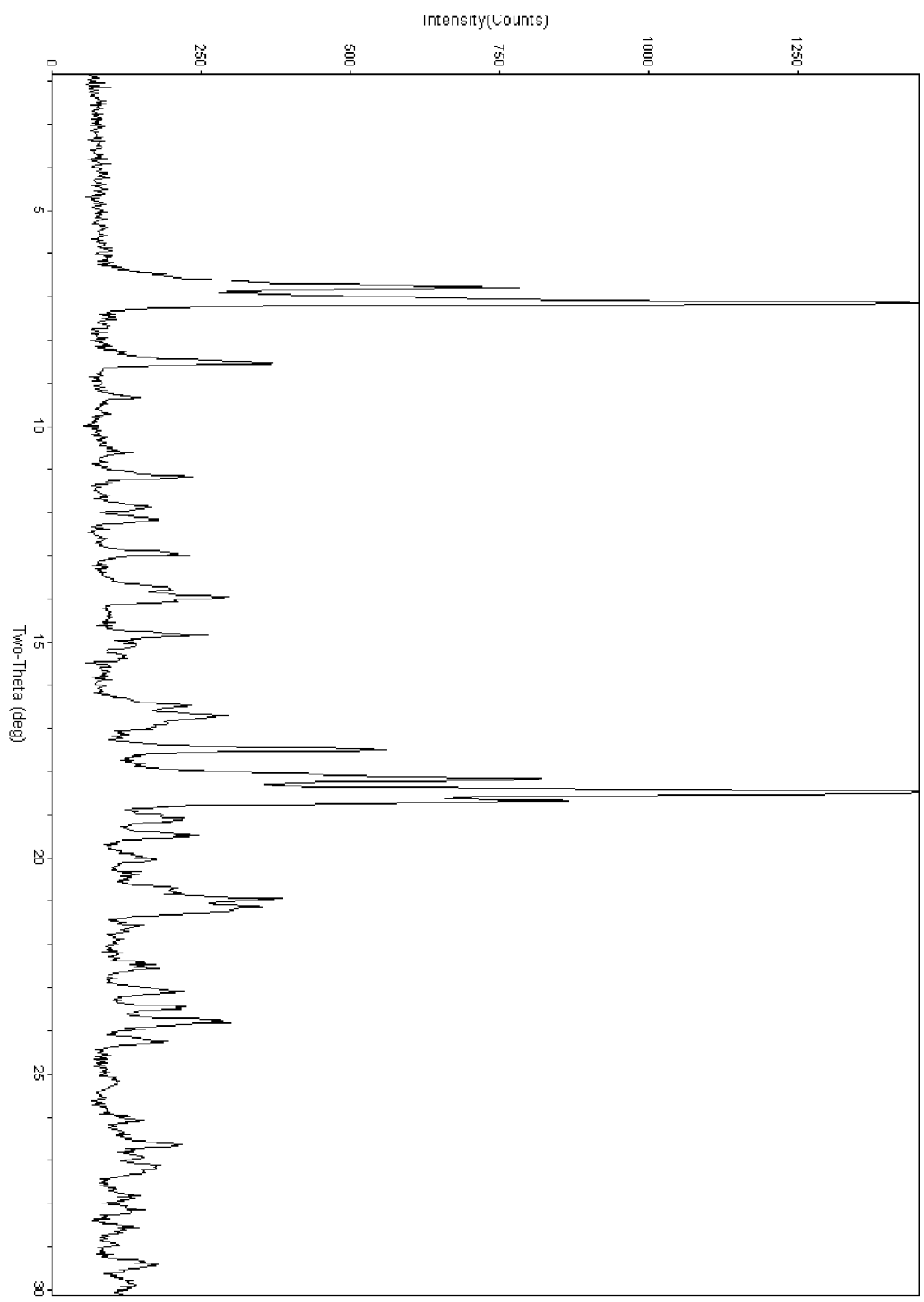
FIG. 1 is a PXRD scan of crystalline Form I ABT-263 bis-HCl.

ABT-263 has at least two protonatable nitrogen atoms and is consequently capable of forming acid addition salts with more than one, for example about 1.2 to about 2, about 1.5 to about 2 or about 1.8 to about 2, equivalents of acid per equivalent of the compound. Illustratively, bis-salts can be formed including acetate, adipate, alginate, bicarbonate, citrate, aspartate, benzoate, besylate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate and undecanoate bis-salts, for example, bis-hydrochloride (bis-HCl) and bis-hydrobromide (bis-HBr) salts.

ABT-263 bis-HCl, which has a molecular weight of 1047.5 g/mol, can be represented by the following structural formula:

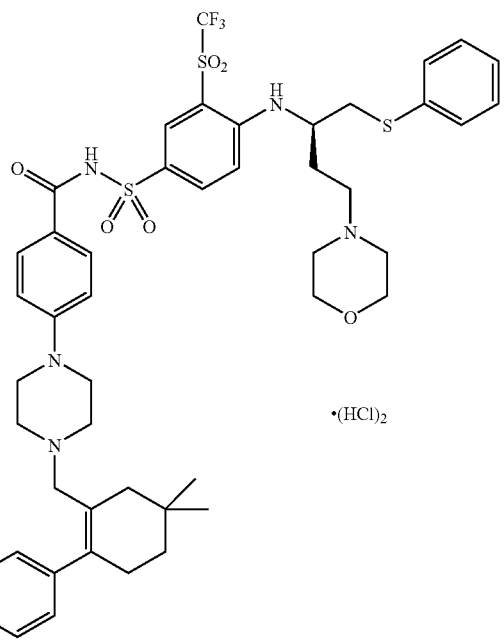

ABT-263 bis-HCl can exist in solid-state form and can be isolated in such a form, for example as illustrated hereinbelow. For use as an API, ABT-263 bis-HCl should be substantially pure, for example at least about 90%, at least about 95%, at least about 96%, at least about 97%, at least about 98%, or at least about 99% pure, by weight. A solid-state form of ABT-263 bis-HCl can be crystalline or amorphous. ABT-263 bis-HCl can also exist in solubilized form in a suitable solubilizing medium, for example as illustrated hereinbelow. Concentration of ABT-263 bis-HCl (expressed as free base equivalent) in such a medium can be, for example, at least about 0.1 mg/ml, at least about 0.2 mg/ml, at least about 0.5 mg/ml, at least about 1 mg/ml, at least about 2 mg/ml or at least about 5 mg/ml, up to the limit of solubility in that medium, for example up to about 500 mg/ml, up to about 400 mg/ml, up to about 300 mg/ml, up to about 200 mg/ml or up to about 100 mg/ml.

ABT-263 bis-HCl can be prepared by any process that comprises reacting ABT-263 free base with 2 moles of hydrochloric acid (HCl) in a suitable medium. The term "free base" is used for convenience herein to refer to ABT-263 parent compound, while recognizing that the parent compound is, strictly speaking, zwitterionic and thus does not always behave as a true base.

ABT-263 free base can be prepared as described in Example 1 of above-cited U.S. Patent Application Publication No. 2007/0027135, the entire disclosure of which is incorporated by reference herein.

An illustrative process for preparing ABT-263 bis-HCl is described below.

The first stage of the process involves the following reaction to prepare ABT-263 parent compound:

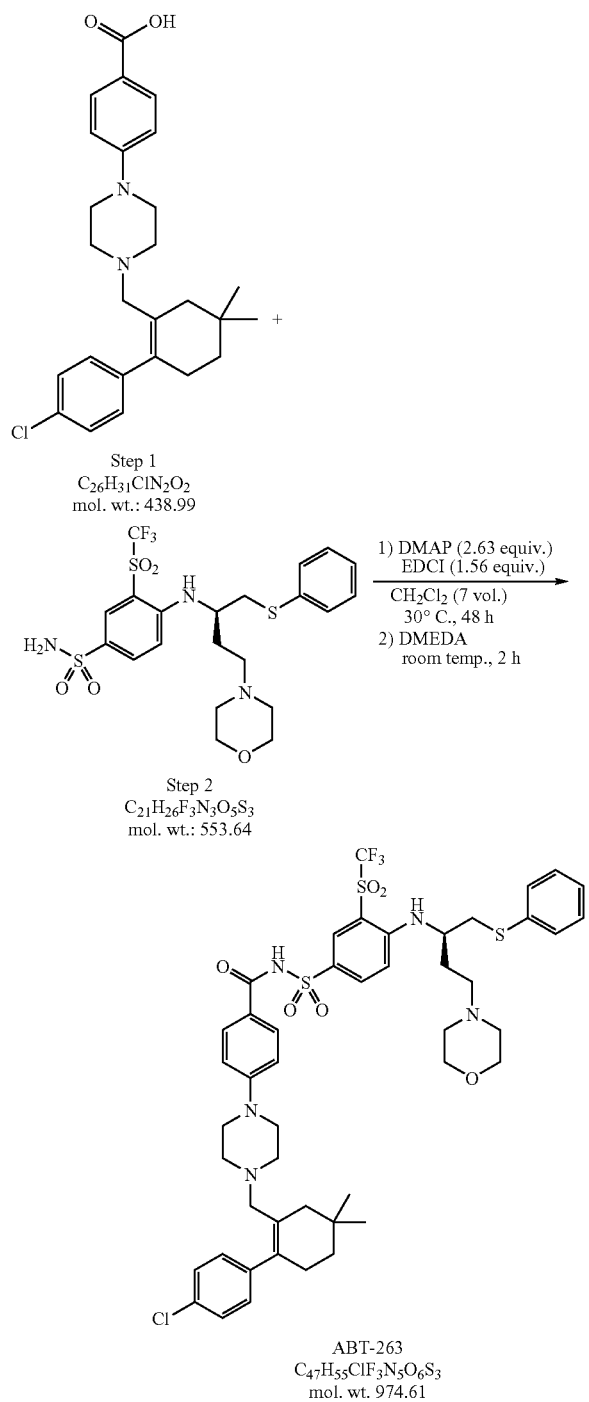

wherein the "Step 1" and "Step 2" products are the intermediates prepared according to Examples 1M and 1I respectively of the '135 publication. "DMAP" is N,N-dimethylamino-pyridine. "EDCI" is 1-(3-dimethylaminopropyl)-3-ethylcarbodiimide. "DMEDA" is N,N-dimethyl ethylenediamine. ABT-263 parent compound is not recovered as a solid product from the reaction mixture.

More particularly, the Step 2 product (13.3 kg, 20.46 mol), the Step 1 product (9.9 kg, 22.5 mol), DMAP (6.6 kg, 53.81 mol) and EDCI hydrochloride (6.12 kg, 31.92 mol) are charged to a reactor. Dichloromethane (126 kg) is then charged, and the resulting reaction mixture is heated at 30° C. until the reaction is complete (about 24 hours; Step 2 product remaining <0.3%). The reaction can be monitored by reverse-phase HPLC.

The reaction mixture is cooled to room temperature, and excess activated acid is quenched by adding DMEDA (1.62 kg, 18.41 mol).

The reaction mixture is distilled to a volume of approximately 48 liters and charged with 8.0 kg water and 150 kg ethyl acetate (EtOAc). The mixture is distilled to a volume of 90 liters and charged with a further 8.0 kg water and 150 kg EtOAc. The mixture is distilled to a volume of 115 liters and charged with 200 kg of a 10% acetic acid+0.75% sodium chloride solution and 100 kg EtOAc. The contents of the reactor are mixed and separated. The organic layer is washed with 200 kg of 10% acetic acid+0.75% sodium chloride solution, 267 kg of 25% $K_2HPO_4$ solution and 242 kg of pH 7 buffer solution.

The organic layer is concentrated to approximately 48 liters, chase-distilled with two portions of EtOAc (180 kg, 180 kg), concentrating to approximately 48 liters each time. Additional EtOAc (85 kg) is charged, and water content is measured by Karl Fischer titration.

The resulting EtOAc solution is diluted with ethanol (EtOH, 62 kg) and polish-filtered through a polypropylene 0.5 μm filter into a clean reactor using EtOAc (20 kg) as a rinse. In a separate portable reactor, a solution of HCl (4.3 kg) in EtOH (80 kg) is prepared and polish-filtered through a separate new filter and housing into the reactor. EtOH (10 kg) is used as a rinse. Polish-filtration of the organic solution removes residual phosphate salts from the final extraction. A clean filter and housing must be used to avoid neutralization of the HCl.

The resulting solution is concentrated to approximately 245 liters and maintained at that volume while an additional chase of EtOH (497 kg) is added. Analysis by HPLC is used to determine whether additional charge of EtOH is necessary to reach the approximately 20 vol needed for crystallization of ABT-263 bis-HCl.

The product solution was heated to 45° C., and ABT-263 bis-HCl crystal seeds (150 g) are added as a slurry in EtOH (1 kg). After 6 hours with agitation at 65 rpm, the slurry is cooled to 20° C. over 1 hour and mixed for another 36 hours. Analysis of the filtrates is performed to indicate completion of crystallization.

The slurry is filtered into a filter-dryer using a polypropylene filter pad. The solids are rinsed with EtOH (2×80 kg). The rinses are applied in a slurry fashion under agitation with no vacuum (contact time 15-25 minutes for each) and then removed by vacuum filtration. The resulting wet cake is sampled for impurities to determine if recrystallization is necessary.

The solids are dried under vacuum and nitrogen at 50° C. for 8 days with mild agitation (5 minutes each hour for the first 8 hours, then 5 minutes each 8-hour shift). Analysis of the dryer sample indicates when drying is complete (<0.05% EtOH remaining).

In a run of the above process, white solid product yield was 17.4 kg (81.0% HPLC peak area yield, 99.72% potency).

The product of this process is crystalline Form I ABT-263 bis-HCl as described more fully below, a substantially solvent-free crystal form prepared by desolvation from an ethanol solvate. This product has been used as API in downstream manufacture of various pharmaceutical compositions (formulations).

Solvates of ABT-263 bis-HCl have been prepared from the API as described below.

A measured amount by weight of ABT-263 bis-HCl prepared as above is suspended in 0.5 ml of each of the solvents individually, as listed in Table 1. The suspensions are agitated at ambient temperature, protected from light. The resulting solvates are characterized by powder X-ray diffraction (PXRD).

PXRD data were collected using a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromator provided monochromatic radiation. The diffractometer was calibrated using the attenuated direct beam at one-degree intervals. Calibration was checked using a silicon powder line position reference standard (NIST 640c). The instrument was computer-controlled using Symphonix software (Inel Corp., Artenay, France) and the data were analyzed using Jade software (version 6.5, Materials Data, Inc., Livermore, Calif.). The sample was loaded onto an aluminum sample holder and leveled with a glass slide.

TABLE 1

Solvents used to prepare ABT-263 bis-HCl crystalline solvates

| Solvent | Weight of compound (mg) |
| --- | --- |
| ethanol | 274.5 |
| 2-propanol | 249.8 |
| t-butanol | 255.8 |
| 1-propanol | 259.6 |
| 2-butanol | 260.1 |
| nitromethane | 284.5 |
| acetonitrile | 290.7 |
| propionitrile | 295.5 |
| ethyl acetate | 300.6 |
| isopropyl acetate | 301.2 |
| ethyl formate | 293.3 |
| methyl acetate | 256.5 |
| acetone | 250.4 |
| 2-butanone (MEK) | 252.8 |
| methyl isopropyl ketone | 255.5 |
| 1,4-dioxane | 262.4 |
| benzene | 250.1 |
| toluene | 290.2 |
| butyl ether | 289.6 |

Single crystals of some solvates have been prepared for crystallographic analysis.

To prepare single crystals of a propionitrile solvate, ABT-263 bis-HCl prepared as above is suspended in propionitrile at 60° C. The suspension is filtered using a syringe filter, and the filtrate is transferred into a new vial. The vial is placed in a hexane chamber. Single crystals are observed one week later. Crystallographic data for the propionitrile solvate are presented in Table 2.

TABLE 2

Crystallographic information for ABT-263 bis-HCl propionitrile solvate

| Lattice type | triclinic |
| --- | --- |
| Space group | P 1 |
| Cell length a | 13.975 Å |
| Cell length b | 16.988 Å |
| Cell length c | 17.850 Å |
| Cell angle α | 101.816° |
| Cell angle β | 105.892° |
| Cell angle γ | 112.258° |
| Cell volume | 3538.28 Å$^3$ |
| Z | 2 |

To prepare single crystals of a nitromethane solvate, ABT-263 bis-HCl prepared as above is suspended in nitromethane at 60° C. The suspension is filtered using a syringe filter, and the filtrate is transferred into a new vial. The vial is placed in a 2-butanone chamber. Single crystals are observed one week later. Crystallographic data for the nitromethane solvate are presented in Table 3.

TABLE 3

Crystallographic information for ABT-263 bis-HCl nitromethane solvate

| Lattice type | monoclinic |
| --- | --- |
| Cell length a | 31.500 Å |
| Cell length b | 13.812 Å |
| Cell length c | 30.764 Å |
| Cell angle α | 90.000° |
| Cell angle β | 116.205° |
| Cell angle γ | 90.000° |
| Cell volume | 12009.1 Å$^3$ |
| Z | 8 |

To prepare single crystals of an acetonitrile solvate, ABT-263 bis-HCl prepared as above is dissolved in water/acetonitrile 1:99 by volume at an elevated temperature close to its limit of solubility. The resulting clear solution is then allowed to cool naturally to ambient temperature. Single crystals are observed after several days. Crystallographic data for the acetonitrile solvate are presented in Table 4.

TABLE 4

Crystallographic information for ABT-263 bis-HCl acetonitrile solvate

| Lattice type | triclinic |
| --- | --- |
| Space group | P 1 |
| Cell length a | 13.799 Å |
| Cell length b | 15.267 Å |
| Cell length c | 15.971 Å |
| Cell angle α | 112.862° |
| Cell angle β | 108.978° |
| Cell angle γ | 96.294° |
| Cell volume | 2822.21 Å$^3$ |
| Z | 2 |

PXRD peaks for individual solvates are listed in Tables 5-23. Peak positions are typically±0.2 degrees two-theta (° 2θ). In the case of propionitrile, nitromethane and acetonitrile solvates, PXRD peaks are calculated from single crystal structure.

TABLE 5

PXRD peak listing: ABT-263 bis-HCl ethanol solvate

| Peak position (°2θ) | Relative intensity |
| --- | --- |
| 5.7 | 1.3 |
| 6.8 | 53.3 |
| 7.1 | 3.3 |
| 7.9 | 2.5 |
| 9.6 | 6.5 |
| 12.3 | 5.6 |
| 13.6 | 4.5 |
| 15.8 | 9.3 |
| 18.4 | 10.2 |
| 18.6 | 18.6 |
| 19.5 | 13.7 |
| 19.8 | 81.5 |
| 20.0 | 100.0 |

TABLE 6

PXRD peak listing: ABT-263 bis-HCl 2-propanol solvate

| Peak position (°2θ) | Relative intensity |
| --- | --- |
| 6.5 | 11.7 |
| 7.0 | 56.8 |
| 8.0 | 2.5 |
| 12.1 | 5.0 |
| 16.2 | 7.4 |
| 17.1 | 4.8 |
| 17.8 | 4.5 |
| 18.2 | 100.0 |
| 18.5 | 96.1 |
| 18.7 | 38.9 |
| 19.6 | 6.7 |

TABLE 7

PXRD peak listing: ABT-263 bis-HCl t-butanol solvate

| Peak position (°2θ) | Relative intensity |
| --- | --- |
| 6.3 | 8.8 |
| 6.8 | 69.2 |
| 7.9 | 3.3 |
| 11.1 | 6.8 |
| 11.4 | 6.8 |
| 12.2 | 5.6 |
| 13.7 | 5.5 |
| 15.9 | 14.7 |
| 17.6 | 10.1 |
| 18.4 | 100.0 |

TABLE 8

PXRD peak listing: ABT-263 bis-HCl 1-propanol solvate

| Peak position (°2θ) | Relative intensity |
| --- | --- |
| 6.6 | 89.9 |
| 7.1 | 3.7 |
| 7.8 | 3.2 |
| 9.5 | 13.0 |
| 12.1 | 5.7 |
| 13.5 | 5.5 |
| 15.4 | 16.9 |
| 18.1 | 9.5 |
| 18.5 | 20.3 |
| 19.2 | 17.0 |
| 19.5 | 100.0 |
| 21.5 | 14.2 |

TABLE 9

PXRD peak listing: ABT-263 bis-HCl 2-butanol solvate

| Peak position (°2θ) | Relative intensity |
| --- | --- |
| 6.8 | 100.0 |
| 7.9 | 1.2 |
| 9.8 | 11.1 |
| 12.2 | 3.2 |
| 13.6 | 6.0 |
| 15.8 | 10.0 |
| 18.2 | 9.1 |
| 18.5 | 16.6 |
| 19.8 | 80.1 |
| 20.0 | 88.4 |

TABLE 10

PXRD peak listing: ABT-263 bis-HCl nitromethane solvate (calculated from crystal structure)

| Peak position (°2θ) | Relative intensity |
| --- | --- |
| 3.2 | 1.4 |
| 6.2 | 60.1 |
| 6.4 | 100.0 |
| 6.7 | 12.0 |
| 7.1 | 11.9 |
| 8.4 | 57.0 |
| 11.9 | 26.4 |
| 13.4 | 14.5 |
| 14.0 | 9.9 |
| 15.9 | 17.4 |
| 17.1 | 12.4 |
| 17.4 | 38.4 |
| 18.6 | 32.4 |
| 18.7 | 35.2 |
| 20.1 | 38.4 |
| 21.0 | 21.3 |
| 21.7 | 17.8 |

TABLE 11

PXRD peak listing: ABT-263 bis-HCl acetonitrile solvate (calculated from crystal structure)

| Peak position (°2θ) | Relative intensity |
| --- | --- |
| 6.5 | 92.7 |
| 6.8 | 59.5 |
| 7.0 | 29.2 |
| 7.4 | 2.3 |
| 8.2 | 50.4 |
| 9.2 | 6.9 |
| 11.1 | 12.8 |
| 12.1 | 12.4 |
| 13.1 | 17.4 |
| 14.1 | 16.6 |
| 15.4 | 25.6 |
| 15.9 | 26.7 |
| 17.1 | 46.1 |
| 17.8 | 100.0 |
| 18.1 | 81.8 |
| 18.4 | 56.9 |
| 19.1 | 13.3 |
| 20.0 | 19.3 |
| 20.6 | 23.2 |
| 21.2 | 75.7 |
| 21.7 | 17.2 |

TABLE 12

PXRD peak listing: ABT-263 bis-HCl propionitrile solvate (calculated from crystal structure)

| Peak position (°2θ) | Relative intensity |
| --- | --- |
| 5.5 | 100.0 |
| 6.0 | 3.0 |
| 6.6 | 9.3 |
| 7.1 | 17.0 |
| 7.3 | 14.1 |
| 8.4 | 1.0 |
| 9.4 | 3.4 |
| 12.7 | 4.9 |
| 14.2 | 4.8 |
| 14.6 | 4.5 |
| 15.7 | 6.3 |
| 18.0 | 6.6 |
| 18.3 | 7.8 |
| 20.6 | 4.6 |

TABLE 13

PXRD peak listing: ABT-263 bis-HCl ethyl acetate solvate

| Peak position (°2θ) | Relative intensity |
|---|---|
| 6.7 | 100.0 |
| 7.2 | 3.2 |
| 8.0 | 6.4 |
| 9.6 | 21.9 |
| 12.4 | 13.2 |
| 13.5 | 7.3 |
| 13.7 | 10.3 |
| 15.1 | 9.2 |
| 15.8 | 15.0 |
| 17.3 | 10.9 |
| 18.5 | 50.1 |
| 19.8 | 94.3 |
| 20.0 | 97.5 |
| 22.1 | 20.0 |
| 24.5 | 11.2 |

TABLE 14

PXRD peak listing: ABT-263 bis-HCl isopropyl acetate solvate

| Peak position (°2θ) | Relative intensity |
|---|---|
| 6.6 | 73.3 |
| 7.8 | 2.7 |
| 9.5 | 15.2 |
| 12.0 | 4.8 |
| 13.4 | 5.9 |
| 14.7 | 6.9 |
| 15.4 | 5.0 |
| 18.1 | 15.6 |
| 18.4 | 22.4 |
| 19.3 | 100.0 |

TABLE 15

PXRD peak listing: ABT-263 bis-HCl ethyl formate solvate

| Peak position (°2θ) | Relative intensity |
|---|---|
| 5.7 | 1.6 |
| 6.8 | 85.8 |
| 7.2 | 3.8 |
| 8.0 | 4.5 |
| 9.7 | 13.9 |
| 12.3 | 9.7 |
| 13.7 | 8.9 |
| 15.9 | 15.7 |
| 18.6 | 46.9 |
| 19.6 | 18.4 |
| 19.9 | 100.0 |
| 22.0 | 21.7 |

TABLE 16

PXRD peak listing: ABT-263 bis-HCl methyl acetate solvate

| Peak position (°2θ) | Relative intensity |
|---|---|
| 6.7 | 23.1 |
| 7.0 | 57.2 |
| 8.2 | 4.0 |
| 11.8 | 10.0 |
| 16.3 | 6.4 |
| 16.8 | 5.5 |
| 17.5 | 3.6 |
| 18.1 | 85 |
| 18.3 | 100.0 |
| 18.7 | 19.1 |
| 21.1 | 19.1 |

TABLE 17

PXRD peak listing: ABT-263 bis-HCl acetone solvate

| Peak position (°2θ) | Relative intensity |
|---|---|
| 6.9 | 63.2 |
| 8.2 | 3.4 |
| 11.8 | 5.6 |
| 12.1 | 2.5 |
| 16.3 | 10.7 |
| 16.7 | 9.8 |
| 17.8 | 14.8 |
| 18.2 | 100.0 |
| 18.4 | 63.3 |
| 20.8 | 20.2 |
| 21.1 | 14.1 |

TABLE 18

PXRD peak listing: ABT-263 bis-HCl MEK solvate

| Peak position (°2θ) | Relative intensity |
|---|---|
| 6.2 | 100.0 |
| 8.2 | 4.3 |
| 10.4 | 6.3 |
| 13.1 | 8.8 |
| 17.0 | 39.1 |
| 17.2 | 38.8 |
| 18.3 | 14.7 |
| 18.8 | 9.4 |

TABLE 19

PXRD peak listing: ABT-263 bis-HCl methyl isopropyl ketone solvate

| Peak position (°2θ) | Relative intensity |
|---|---|
| 6.5 | 100.0 |
| 7.8 | 1.6 |
| 9.3 | 15.9 |
| 12.3 | 6.5 |
| 13.3 | 4.7 |
| 14.8 | 5.3 |
| 15.6 | 5.7 |
| 18.0 | 26.4 |
| 18.4 | 8.1 |
| 19.1 | 50.0 |
| 19.5 | 64.2 |

TABLE 20

PXRD peak listing: ABT-263 bis-HCl 1,4-dioxane solvate

| Peak position (°2θ) | Relative intensity |
|---|---|
| 5.7 | 100.0 |
| 7.0 | 3.1 |
| 7.5 | 2.9 |
| 15.3 | 6.8 |
| 16.0 | 5.0 |
| 17.0 | 11.4 |
| 17.8 | 5.8 |
| 18.4 | 17.7 |
| 18.6 | 28.6 |
| 19.5 | 32.4 |
| 20.4 | 9.1 |
| 21.3 | 22.1 |

TABLE 21

PXRD peak listing: ABT-263 bis-HCl benzene solvate

| Peak position (°2θ) | Relative intensity |
|---|---|
| 5.3 | 100.0 |
| 5.7 | 53.9 |
| 6.5 | 25.9 |
| 6.8 | 46.5 |
| 7.2 | 45.6 |
| 17.9 | 48.1 |
| 18.2 | 80.4 |
| 18.6 | 85.7 |
| 19.3 | 12.2 |
| 19.6 | 14.9 |
| 20.2 | 15.3 |
| 20.7 | 15.3 |
| 21.0 | 23.6 |
| 21.3 | 21.4 |

TABLE 22

PXRD peak listing: ABT-263 bis-HCl toluene solvate

| Peak position (°2θ) | Relative intensity |
|---|---|
| 5.5 | 100.0 |
| 6.7 | 14.5 |
| 7.0 | 5.9 |
| 7.9 | 4.4 |
| 9.3 | 3.9 |
| 10.7 | 7.2 |
| 14.1 | 13.5 |
| 14.7 | 8.8 |
| 17.8 | 41.2 |
| 18.0 | 42.0 |
| 18.5 | 17.1 |
| 19.3 | 36.6 |
| 19.8 | 16.0 |

TABLE 23

PXRD peak listing: ABT-263 bis-HCl butyl ether solvate

| Peak position (°2θ) | Relative intensity |
|---|---|
| 6.7 | 28 |
| 7.0 | 60.6 |
| 8.4 | 9.8 |
| 11.8 | 5.9 |
| 12.2 | 3.5 |
| 13.5 | 5.3 |
| 16.5 | 8.0 |
| 16.7 | 10.8 |
| 17.9 | 39.7 |
| 18.4 | 100.0 |
| 20.7 | 15.4 |
| 20.8 | 17.1 |
| 21.2 | 23.1 |

Desolvation of most solvates, including 1-propanol, 2-propanol, 2-butanol, t-butanol, acetonitrile, propionitrile, ethyl formate, methyl acetate, ethyl acetate, isopropyl acetate, acetone, methyl isopropyl ketone, 1,4-dioxane, benzene, toluene and butyl ether solvates, provides a solvent-free crystal form of ABT-263 bis-HCl that is shown by PXRD to be identical to that of the API produced by desolvation of the ethanol solvate. This crystal form is designated Form I. A PXRD scan of Form I ABT-263 bis-HCl is shown in FIG. 1. PXRD peaks for Form I ABT-263 bis-HCl are listed in Table 24. A PXRD pattern having peaks substantially as indicated therein can be used to identify ABT-263 bis-HCl, more particularly Form I ABT-263 bis-HCl. The phrase "substantially as indicated" in the present context means having peaks that are not shifted more than about 0.2° 2θ from the indicated position. It will be recognized that relative intensity of peaks can be somewhat variable from run to run, but in general the ranking of peaks in intensity is similar to that of the PXRD pattern shown in Table 24.

TABLE 24

PXRD peak listing: ABT-263 bis-HCl Form I

| Peak position (°2θ) | Relative intensity |
|---|---|
| 6.8 | 59.0 |
| 7.2 | 75.9 |
| 8.5 | 14.3 |
| 9.3 | 4.3 |
| 11.2 | 6.5 |
| 13.8 | 15.8 |
| 14.0 | 17.7 |
| 14.9 | 9.5 |
| 16.7 | 17.5 |
| 17.5 | 15.7 |
| 18.2 | 52.2 |
| 18.5 | 100.0 |
| 18.7 | 95.4 |

Form I ABT-263 bis-HCl can generally be distinguished from Form II below by presence of any one or more, for example any two or more, any three or more, any four or more, or all five, of the following PXRD peaks: 6.8, 7.2, 8.5, 18.5 and 18.7° 2θ, in each case ±0.2° 2θ.

Figure 2:
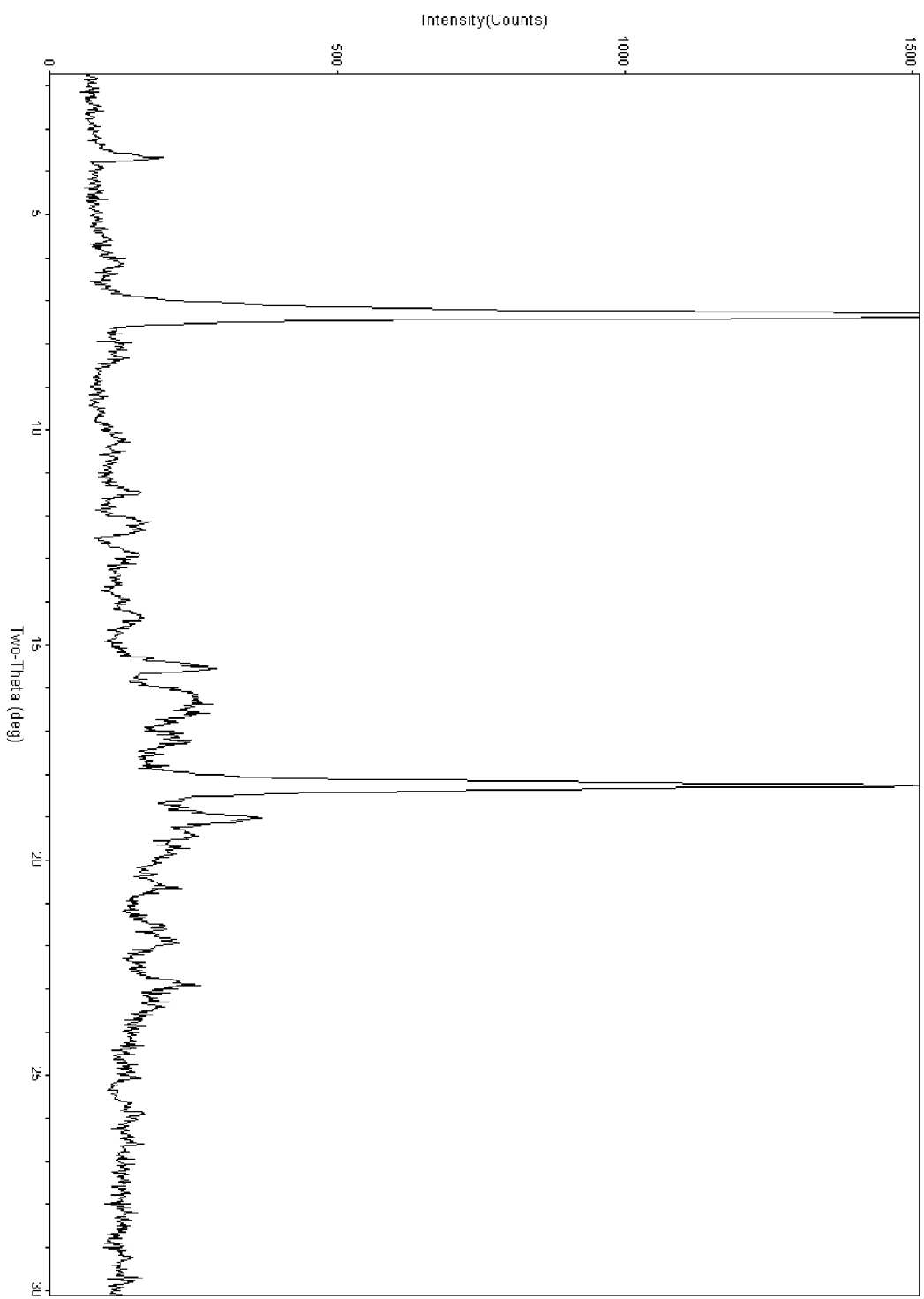
FIG. 2 is a PXRD scan of crystalline Form II ABT-263 bis-HCl.

Desolvation of the MEK solvate provides a solvent-free crystal form of ABT-263 bis-HCl that is shown by PXRD to be different from that of the API produced by desolvation of the ethanol solvate. This crystal form derived from desolvation of the MEK solvate is designated Form II. A PXRD scan of Form II ABT-263 bis-HCl is shown in FIG. 2. PXRD peaks for Form II ABT-263 bis-HCl are listed in Table 25. A PXRD pattern having peaks substantially as indicated therein can be used to identify ABT-263 bis-HCl, more particularly Form II ABT-263 bis-HCl. The phrase "substantially as indicated" in the present context means having peaks that are not shifted more than about 0.2° 2θ from the indicated position. It will be recognized that relative intensity of peaks can be somewhat variable from run to run, but in general the ranking of peaks in intensity is similar to that of the PXRD pattern shown in Table 25.

TABLE 25

PXRD peak listing: ABT-263 bis-HCl Form II

| Peak position (°2θ) | Relative intensity |
|---|---|
| 3.7 | 6.0 |
| 7.4 | 100.0 |
| 12.1 | 5.3 |
| 15.6 | 8.6 |
| 16.1 | 16.2 |
| 16.6 | 21.6 |
| 18.3 | 70.2 |
| 19.0 | 13.4 |

Form II ABT-263 bis-HCl can generally be distinguished from Form I above by presence of either or both of the following PXRD peaks: 3.7 and 7.4° 2θ, in each case ±0.2° 2θ.

ABT-263 bis-HCl, for example Form I, Form II or a combination thereof, can be used in preparation of pharmaceutical compositions suitable for any route of administration, including oral, to a subject in need thereof Thus in some embodiments of the present invention, a pharmaceutical composition is provided, comprising ABT-263 bis-HCl and one or more pharmaceutically acceptable excipients. In one embodiment, the composition comprises Form I ABT-263 bis-HCl. In another embodiment, the composition comprises Form II ABT-263 bis-HCl. In yet another embodiment, the composition comprises a solution of ABT bis-HCl in a suitable carrier system. According to any of these embodiments, the composition can be deliverable, for example, by the oral route. Other routes of administration include without limitation parenteral, sublingual, buccal, intranasal, pulmonary, topical, transdermal, intradermal, ocular, otic, rectal, vaginal, intragastric, intracranial, intrasynovial and intra-articular routes.

Such compositions comprise ABT-263 bis-HCl in an amount that can be therapeutically effective when the composition is administered to a subject in need thereof according to an appropriate regimen. Dosage amounts are expressed herein as free base equivalent amounts unless the context requires otherwise. Typically, a unit dose (the amount administered at a single time), which can be administered at an appropriate frequency, e.g., twice daily to once weekly, is about 10 to about 1,000 mg. Where frequency of administration is once daily (q.d.), unit dose and daily dose are the same. Illustratively, the unit dose of ABT-263 in a composition of the invention can be about 25 to about 1,000 mg, more typically about 50 to about 500 mg, for example about 50, about 100, about 150, about 200, about 250, about 300, about 350, about 400, about 450 or about 500 mg. Where the composition is prepared as a discrete dosage form such as a tablet or capsule, a unit dose can be deliverable in a single dosage form or a small plurality of dosage forms, most typically 1 to about 10 dosage forms.

The higher the unit dose, the more desirable it becomes to select excipients that permit a relatively high loading of API (in this case ABT-263 bis-HCl) in the formulation. Typically, the concentration of ABT-263 bis-HCl in a formulation of the invention (expressed as free base equivalent) is at least about 1%, e.g., about 1% to about 50%, by weight, but lower and higher concentrations can be acceptable or achievable in specific cases. Illustratively, the ABT-263 free base equivalent concentration in various embodiments is at least about 2%, e.g., about 2% to about 40%, by weight, for example about 5%, about 10%, about 15%, about 20%, about 25% or about 30% by weight of the formulation.

A composition of the invention comprises, in addition to the API, one or more pharmaceutically acceptable excipients. If the composition is to be prepared in solid form for oral administration, for example as a tablet or capsule, it typically includes at least one or more solid diluents and one or more solid disintegrants. Optionally, the excipients further include one or more binding agents, wetting agents and/or antifrictional agents (lubricants, anti-adherents and/or glidants). Many excipients have two or more functions in a pharmaceutical composition. Characterization herein of a particular excipient as having a certain function, e.g., diluent, disintegrant, binding agent, etc., should not be read as limiting to that function. Further information on excipients can be found in standard reference works such as *Handbook of Pharmaceutical Excipients*, 3rd ed. (Kibbe, ed. (2000), Washington: American Pharmaceutical Association).

Suitable diluents illustratively include, either individually or in combination, lactose, including anhydrous lactose and lactose monohydrate; lactitol; maltitol; mannitol; sorbitol; xylitol; dextrose and dextrose monohydrate; fructose; sucrose and sucrose-based diluents such as compressible sugar, confectioner's sugar and sugar spheres; maltose; inositol; hydrolyzed cereal solids; starches (e.g., corn starch, wheat starch, rice starch, potato starch, tapioca starch, etc.), starch components such as amylose and dextrates, and modified or processed starches such as pregelatinized starch; dextrins; celluloses including powdered cellulose, microcrystalline cellulose, silicified microcrystalline cellulose, food grade sources of α- and amorphous cellulose and powdered cellulose, and cellulose acetate; calcium salts including calcium carbonate, tribasic calcium phosphate, dibasic calcium phosphate dihydrate, monobasic calcium sulfate monohydrate, calcium sulfate and granular calcium lactate trihydrate; magnesium carbonate; magnesium oxide; bentonite; kaolin; sodium chloride; and the like. Such diluents, if present, typically constitute in total about 5% to about 95%, for example about 20% to about 90%, or about 50% to about 85%, by weight of the composition. The diluent or diluents selected preferably exhibit suitable flow properties and, where tablets are desired, compressibility.

Microcrystalline cellulose and silicified microcrystalline cellulose are particularly useful diluents, and are optionally used in combination with a water-soluble diluent such as mannitol. Illustratively, a suitable weight ratio of microcrystalline cellulose or silicified microcrystalline cellulose to mannitol is about 10:1 to about 1:1, but ratios outside this range can be useful in particular circumstances.

Suitable disintegrants include, either individually or in combination, starches including pregelatinized starch and sodium starch glycolate; clays; magnesium aluminum silicate; cellulose-based disintegrants such as powdered cellulose, microcrystalline cellulose, methylcellulose, low-substituted hydroxypropylcellulose, carmellose, carmellose calcium, carmellose sodium and croscarmellose sodium; alginates; povidone; crospovidone; polacrilin potassium; gums such as agar, guar, locust bean, karaya, pectin and tragacanth gums; colloidal silicon dioxide; and the like. One or more disintegrants, if present, typically constitute in total about 0.2% to about 30%, for example about 0.5% to about 20%, or about 1% to about 10%, by weight of the composition.

Sodium starch glycolate is a particularly useful disintegrant, and typically constitutes in total about 1% to about 20%, for example about 2% to about 15%, or about 5% to about 10%, by weight of the composition.

Binding agents or adhesives are useful excipients, particularly where the composition is in the form of a tablet. Such binding agents and adhesives should impart sufficient cohesion to the blend being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; glucose; polydextrose; starch including pregelatinized starch; gelatin; modified celluloses including methylcellulose, carmellose sodium, hydroxypropylmethylcellulose (HPMC), hydroxypropylcellulose, hydroxyethylcellulose and ethylcellulose; dextrins including maltodextrin; zein; alginic acid and salts of alginic acid, for example sodium alginate; magnesium aluminum silicate; bentonite; polyethylene glycol (PEG); polyethylene oxide; guar gum; polysaccharide acids; polyvinylpyrrolidone (povidone or PVP), for example povidone K-15, K-30 and K-29/32; polyacrylic acids (carbomers); polymethacrylates; and the like. One or more binding agents and/or adhesives, if present, typically constitute in total about 0.5% to about 25%, for example about 1% to about 15%, or about 1.5% to about 10%, by weight of the composition.

Povidone and hydroxypropylcellulose, either individually or in combination, are particularly useful binding agents for tablet formulations, and, if present, typically constitute about 0.5% to about 15%, for example about 1% to about 10%, or about 2% to about 8%, by weight of the composition.

Wetting agents, if present, are normally selected to maintain the drug in close association with water, a condition that can improve bioavailability of the composition. Non-limiting examples of surfactants that can be used as wetting agents include, either individually or in combination, quaternary ammonium compounds, for example benzalkonium chloride, benzethonium chloride and cetylpyridinium chloride; dioctyl sodium sulfosuccinate; polyoxyethylene alkylphenyl ethers, for example nonoxynol 9, nonoxynol 10 and octoxynol 9; poloxamers (polyoxyethylene and polyoxypropylene block copolymers); polyoxyethylene fatty acid glycerides and oils, for example polyoxyethylene (8) caprylic/capric mono- and diglycerides, polyoxyethylene (35) castor oil and polyoxyethylene (40) hydrogenated castor oil; polyoxyethylene alkyl ethers, for example ceteth-10, laureth-4, laureth-23, oleth-2, oleth-10, oleth-20, steareth-2, steareth-10, steareth-20, steareth-100 and polyoxyethylene (20) cetostearyl ether; polyoxyethylene fatty acid esters, for example polyoxyethylene (20) stearate, polyoxyethylene (40) stearate and polyoxyethylene (100) stearate; sorbitan esters, for example sorbitan monolaurate, sorbitan monooleate, sorbitan monopalmitate and sorbitan monostearate; polyoxyethylene sorbitan esters, for example polysorbate 20 and polysorbate 80; propylene glycol fatty acid esters, for example propylene glycol laurate; sodium lauryl sulfate; fatty acids and salts thereof, for example oleic acid, sodium oleate and triethanolamine oleate; glyceryl fatty acid esters, for example glyceryl monooleate, glyceryl monostearate and glyceryl palmitostearate; tyloxapol; and the like. One or more wetting agents, if present, typically constitute in total about 0.1% to about 15%, for example about 0.2% to about 10%, or about 0.5% to about 7%, by weight of the composition.

Nonionic surfactants, more particularly poloxamers, are examples of wetting agents that can be useful herein. Illustratively, a poloxamer such as Pluronic™ F127, if present, can constitute about 0.1% to about 10%, for example about 0.2% to about 7%, or about 0.5% to about 5%, by weight of the composition.

Lubricants reduce friction between a tableting mixture and tableting equipment during compression of tablet formulations. Suitable lubricants include, either individually or in combination, glyceryl behenate; stearic acid and salts thereof, including magnesium, calcium and sodium stearates; hydrogenated vegetable oils; glyceryl palmitostearate; talc; waxes; sodium benzoate; sodium acetate; sodium fumarate; sodium stearyl fumarate; PEGs (e.g., PEG 4000 and PEG 6000); poloxamers; polyvinyl alcohol; sodium oleate; sodium lauryl sulfate; magnesium lauryl sulfate; and the like. One or more lubricants, if present, typically constitute in total about 0.05% to about 10%, for example about 0.1% to about 5%, or about 0.2% to about 2%, by weight of the composition. Sodium stearyl fumarate is a particularly useful lubricant.

Anti-adherents reduce sticking of a tablet formulation to equipment surfaces. Suitable anti-adherents include, either individually or in combination, talc, colloidal silicon dioxide, starch, DL-leucine, sodium lauryl sulfate and metallic stearates. One or more anti-adherents, if present, typically constitute in total about 0.05% to about 10%, for example about 0.1% to about 7%, or about 0.2% to about 5%, by weight of the composition. Colloidal silicon dioxide is a particularly useful anti-adherent.

Glidants improve flow properties and reduce static in a tableting mixture. Suitable glidants include, either individually or in combination, colloidal silicon dioxide, starch, powdered cellulose, sodium lauryl sulfate, magnesium trisilicate and metallic stearates. One or more glidants, if present, typically constitute in total about 0.05% to about 10%, for example about 0.1% to about 7%, or about 0.2% to about 5%, by weight of the composition. Colloidal silicon dioxide is a particularly useful glidant.

Other excipients such as buffering agents, stabilizers, antioxidants, antimicrobials, colorants, flavors and sweeteners are known in the pharmaceutical art and can be used in compositions of the present invention. Tablets can be uncoated or can comprise a core that is coated, for example with a nonfunctional film or a release-modifying or enteric coating. Capsules can have hard or soft shells comprising, for example, gelatin (in the form of hard gelatin capsules or soft elastic gelatin capsules), starch, carrageenan and/or HPMC, optionally together with one or more plasticizers.

A solid orally deliverable composition of the present invention is not limited by any process used to prepare it. Any suitable process of pharmacy can be used, including dry blending with or without direct compression, and wet or dry granulation.

If the composition is to be prepared in liquid (including encapsulated liquid) form, the API (ABT-263 bis-HCl) can be, for example, dissolved in a suitable carrier, typically one comprising a lipid solvent for the API. The higher the unit dose, the more desirable it becomes to select a carrier that permits a relatively high concentration of the drug in solution therein. Typically, the free base equivalent concentration of API in the carrier is at least about 10 mg/ml, e.g., about 10 to about 500 mg/ml, but lower and higher concentrations can be acceptable or achievable in specific cases. Illustratively, the drug concentration in various embodiments is at least about 10 mg/ml, e.g., about 10 to about 400 mg/ml, or at least about 20 mg/ml, e.g., about 20 to about 200 mg/ml, for example about 20, about 25, about 30, about 40, about 50, about 75, about 100, about 125, about 150 or about 200 mg/ml.

The carrier can be substantially non-aqueous, i.e., having no water, or having an amount of water that is small enough to be, in practical terms, essentially non-deleterious to performance or properties of the composition. Typically, the carrier comprises zero to less than about 5% by weight water. It will be understood that certain ingredients useful herein can bind small amounts of water on or within their molecules or supramolecular structures; such bound water if present does not affect the "substantially non-aqueous" character of the carrier as defined herein.

In some embodiments, the carrier comprises one or more glyceride materials. Suitable glyceride materials include, without limitation, medium to long chain mono-, di- and triglycerides. The term "medium chain" herein refers to hydrocarbyl chains individually having no less than about 6 and less than about 12 carbon atoms, including for example $C_8$ to $C_{10}$ chains. Thus glyceride materials comprising capryl and capryl chains, e.g., caprylic/capric mono-, di- and/or triglycerides, are examples of "medium chain" glyceride materials herein. The term "long chain" herein refers to hydrocarbyl chains individually having at least about 12, for example about 12 to about 18, carbon atoms, including for example lauryl, myristyl, cetyl, stearyl, oleyl, linoleyl and linolenyl chains. Medium to long chain hydrocarbyl groups in the glyceride materials can be saturated, mono- or polyunsaturated.

In one embodiment the carrier comprises a medium chain and/or a long chain triglyceride material. A suitable example of a medium chain triglyceride material is a caprylic/capric triglyceride product such as, for example, Captex 355 EP™ of Abitec Corp. and products substantially equivalent thereto. Suitable examples of long chain triglycerides include any pharmaceutically acceptable vegetable oil, for example canola, coconut, corn, cottonseed, flaxseed, olive, palm, peanut, safflower, sesame, soy and sunflower oils, and mixtures of such oils. Oils of animal, particularly marine animal, origin can also be used, including for example fish oil.

A carrier system that has been found particularly useful comprises two essential components: a phospholipid, and a pharmaceutically acceptable solubilizing agent for the phospholipid. It will be understood that reference in the singular to a (or the) phospholipid, solubilizing agent or other formulation ingredient herein includes the plural; thus combinations, for example mixtures, of more than one phospholipid, or more than one solubilizing agent, are expressly contemplated herein. The solubilizing agent, or the combination of solubilizing agent and phospholipid, also solubilizes the drug, although other carrier ingredients, such as a surfactant or an alcohol such as ethanol, optionally present in the carrier can in some circumstances provide enhanced solubilization of the drug.

Any pharmaceutically acceptable phospholipid or mixture of phospholipids can be used. In general such phospholipids are phosphoric acid esters that yield on hydrolysis phosphoric acid, fatty acid(s), an alcohol and a nitrogenous base. Pharmaceutically acceptable phospholipids can include without limitation phosphatidylcholines, phosphatidylserines and phosphatidylethanolamines. In one embodiment the composition comprises phosphatidylcholine, derived for example from natural lecithin. Any source of lecithin can be used, including animal sources such as egg yolk, but plant sources are generally preferred. Soy is a particularly rich source of lecithin that can provide phosphatidylcholine for use in the present invention.

Illustratively, a suitable amount of phospholipid is about 15% to about 75%, for example about 30% to about 60%, by weight of the carrier, although greater and lesser amounts can be useful in particular situations.

Ingredients useful as components of the solubilizing agent are not particularly limited and will depend to some extent on the desired concentration of drug and of phospholipid. In one embodiment, the solubilizing agent comprises one or more glycols, one or more glycolides and/or one or more glyceride materials.

Suitable glycols include propylene glycol and polyethylene glycols (PEGs) having molecular weight of about 200 to about 1,000 g/mol, e.g., PEG-400, which has an average molecular weight of about 400 g/mol. Such glycols can provide relatively high solubility of the drug; however the potential for oxidative degradation of the drug can be increased when in solution in a carrier comprising such glycols, for example because of the tendency of glycols to produce superoxides, peroxides and/or free hydroxyl radicals. The higher the glycol content of the carrier, the greater may be the tendency for degradation of a chemically unstable drug. In one embodiment, therefore, one or more glycols are present in a total glycol amount of at least about 1% but less than about 50%, for example less than about 30%, less than about 20%, less than about 15% or less than about 10% by weight of the carrier. In another embodiment, the carrier comprises substantially no glycol.

Glycolides are glycols such as propylene glycol or PEG esterified with one or more organic acids, for example medium- to long-chain fatty acids. Suitable examples include propylene glycol monocaprylate, propylene glycol monolaurate and propylene glycol dilaurate products such as, for example, Capmul PG-8™, Capmul PG-12™ and Capmul PG-2L™ respectively of Abitec Corp. and products substantially equivalent thereto.

Suitable glyceride materials for use together with a phospholipid include, without limitation, those mentioned above. Where one or more glyceride materials are present as a major component of the solubilizing agent, a suitable total amount of glycerides is an amount effective to solubilize the phospholipid and, in combination with other components of the carrier, effective to maintain the drug and antioxidant in solution. For example, glyceride materials such as medium chain and/or long chain triglycerides can be present in a total glyceride amount of about 5% to about 70%, for example about 15% to about 60% or about 25% to about 50%, by weight of the carrier.

Additional solubilizing agents that are other than glycols or glyceride materials can be included if desired. Such agents, for example N-substituted amide solvents such as dimethylformamide (DMF) and N,N-dimethylacetamide (DMA), can, in specific cases, assist in raising the limit of solubility of the drug in the carrier, thereby permitting increased drug loading. However, the carriers useful herein generally provide adequate solubility of small-molecule drugs of interest herein without such additional agents.

Even when a sufficient amount of a glycol, glycolide or glyceride material is present to solubilize the phospholipid, the resulting carrier solution and/or the drug-carrier system may be rather viscous and difficult or inconvenient to handle. In such cases it may be found desirable to include in the carrier a viscosity reducing agent in an amount effective to provide acceptably low viscosity. An example of such an agent is an alcohol, more particularly ethanol, which is preferably introduced in a form that is substantially free of water, for example 99% ethanol, dehydrated alcohol USP or absolute ethanol. Excessively high concentrations of ethanol should, however, generally be avoided. This is particularly true where, for example, the drug-carrier system is to be administered in a gelatin capsule, because of the tendency of high ethanol concentrations to result in mechanical failure of the capsule. In general, suitable amounts of ethanol are 0% to about 25%, for example about 1% to about 20% or about 3% to about 15%, by weight of the carrier.

Optionally, the carrier further comprises a pharmaceutically acceptable non-phospholipid surfactant. One of skill in the art will be able to select a suitable surfactant for use in a composition of the invention. Illustratively, a surfactant such as polysorbate 80 can be included in an amount of 0% to about 5%, for example 0% to about 2% or 0% to about 1%, by weight of the carrier.

Conveniently, pre-blended products are available containing a suitable phospholipid+solubilizing agent combination for use in compositions of the present invention. Pre-blended phospholipid+solubilizing agent products can be advantageous in improving ease of preparation of the present compositions.

An illustrative example of a pre-blended phospholipid+solubilizing agent product is Phosal 50 PG™, available from Phospholipid GmbH, Germany, which comprises, by weight, not less than 50% phosphatidylcholine, not more than 6% lysophosphatidylcholine, about 35% propylene glycol, about 3% mono- and diglycerides from sunflower oil, about 2% soy fatty acids, about 2% ethanol, and about 0.2% ascorbyl palmitate.

Another illustrative example is Phosal 53 MCT™, also available from Phospholipid GmbH, which contains, by weight, not less than 53% phosphatidylcholine, not more than 6% lysophosphatidylcholine, about 29% medium chain triglycerides, 3-6% (typically about 5%) ethanol, about 3% mono- and diglycerides from sunflower oil, about 2% oleic acid, and about 0.2% ascorbyl palmitate (reference composition). A product having the above or substantially equivalent composition, whether sold under the Phosal 53 MCT™ brand or otherwise, is generically referred to herein as "phosphatidylcholine+medium chain triglycerides 53/29". A product having "substantially equivalent composition" in the present context means having a composition sufficiently similar to the reference composition in its ingredient list and relative amounts of ingredients to exhibit no practical difference in properties with respect to utilization of the product herein.

Yet another illustrative example is Lipoid S75™, available from Lipoid GmbH, which contains, by weight, not less than 70% phosphatidylcholine in a solubilizing system. This can be further blended with medium-chain triglycerides, for example in a 30/70 weight/weight mixture, to provide a product ("Lipoid S75™ MCT") containing, by weight, not less than 20% phosphatiylcholine, 2-4% phosphatidylethanolamine, not more than 1.5% lysophosphatidylcholine, and 67-73% medium-chain triglycerides.

Yet another illustrative example is Phosal 50 SA+™, also available from Phospholipid GmbH, which contains, by weight, not less than 50% phosphatidylcholine and not more than 6% lysophosphatidylcholine in a solubilizing system comprising safflower oil and other ingredients.

The phosphatidylcholine component of each of these pre-blended products is derived from soy lecithin. Products of substantially equivalent composition may be obtainable from other suppliers.

A pre-blended product such as Phosal 50 PG™, Phosal 53 MCT™, Lipoid S75™ MCT or Phosal 50 SA+™ can, in some embodiments, constitute substantially the entire carrier system. In other embodiments, additional ingredients are present, for example ethanol (additional to any that may be present in the pre-blended product), non-phospholipid surfactant such as polysorbate 80, polyethylene glycol and/or other ingredients. Such additional ingredients, if present, are typically included in only minor amounts. Illustratively, phosphatidylcholine+medium chain triglycerides 53/29 can be included in the carrier in an amount of about 50% to 100%, for example about 80% to 100%, by weight of the carrier.

ABT-263 and its bis-HCl salt are susceptible to degradation in an oxidative environment; thus it will often be found desirable to include an antioxidant in the composition. Antioxidants used in pharmaceutical compositions are most typically agents that inhibit generation of oxidative species such as triplet or singlet oxygen, superoxides, peroxide and free hydroxyl radicals, or agents that scavenge such oxidative species as they are generated. Examples of commonly used antioxidants of these classes include butylated hydroxyanisole (BHA), butylated hydroxytoluene (BHT), retinyl palmitate, tocopherol, propyl gallate, ascorbic acid and ascorbyl palmitate. Such antioxidants can be used; alternatively heavier-chalcogen antioxidants may be particularly useful.

A chalcogen is an element of Group 16 (formerly known as Group VIA) of the periodic table, including oxygen, sulfur, selenium and tellurium. A "heavier-chalcogen" herein means a chalcogen having heavier atomic weight than oxygen, specifically including sulfur and selenium. A "heavier-chalcogen antioxidant" or "HCA" is a compound having antioxidant properties that contains one or more oxidizable sulfur or selenium, most particularly sulfur, atoms. HCAs are believed, without being bound by theory, to function primarily as competitive substrates, i.e., as "sacrificial" antioxidants, which are preferentially attacked by oxidative species thereby protecting the drug from excessive degradation.

In some embodiments, the HCA comprises one or more antioxidant compounds of Formula II:

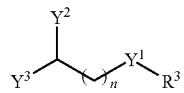

II where
n is 0, 1 or 2;
$Y^1$ is S or Se;
$Y^2$ is $NHR^1$, OH or H, where $R^1$ is alkyl or alkylcarbonyl;
$Y^3$ is $COOR^2$ or $CH_2OH$, where $R^2$ is H or alkyl; and
$R^3$ is H or alkyl;
where alkyl groups are independently optionally substituted with one of more substituents independently selected from the group consisting of carboxyl, alkylcarbonyl, alkoxycarbonyl, amino and alkylcarbonylamino; a pharmaceutically acceptable salt thereof; or, where $Y^1$ is S and $R^3$ is H, an —S—S— dimer thereof or pharmaceutically acceptable salt of such dimer.

In other embodiments, the HCA is an antioxidant compound of Formula III:

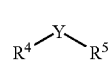

III where
Y is S, Se or S—S; and
$R^4$ and $R^5$ are independently selected from H, alkyl and $(CH_2)_nR^6$ where n is 0-10 and $R^6$ is arylcarbonyl, alkylcarbonyl, alkoxycarbonyl, carboxyl or $CHR^7R^8$-substituted alkyl, where $R^7$ and $R^8$ are independently $CO_2R^9$, $CH_2OH$, hydrogen or $NHR^{10}$, where $R^9$ is H, alkyl, substituted alkyl or arylalkyl and $R^{10}$ is hydrogen, alkyl, alkylcarbonyl or alkoxycarbonyl.

An "alkyl" substituent or an "alkyl" or "alkoxy" group forming part of a substituent according to Formula II or Formula III is one having 1 to about 18 carbon atoms and can consist of a straight or branched chain.

An "aryl" group forming part of a substituent according to Formula III is a phenyl group, unsubstituted or substituted with one or more hydroxy, alkoxy or alkyl groups.

In some embodiments, $R^1$ in Formula II is $C_{1-4}$ alkyl (e.g., methyl or ethyl) or ($C_{1-4}$ alkyl)carbonyl (e.g., acetyl).

In some embodiments, $R^2$ in Formula II is H or $C_{1-18}$ alkyl, for example methyl, ethyl, propyl (e.g., n-propyl or isopropyl), butyl (e.g., n-butyl, isobutyl or t-butyl), octyl (e.g., n-octyl or 2-ethylhexyl), dodecyl (e.g., lauryl), tridecyl, tetradecyl, hexadecyl or octadecyl (e.g., stearyl).

$R^3$ is typically H or $C_{1-4}$ alkyl (e.g., methyl or ethyl).

The HCA can be, for example, a natural or synthetic amino acid or a derivative thereof such as an alkyl ester or N-acyl derivative, or a salt of such amino acid or derivative. Where the amino acid or derivative thereof is derived from a natural source it is typically in the L-configuration; however it is understood that D-isomers and D,L-isomer mixtures can be substituted if necessary.

Non-limiting examples of HCAs useful herein include β-alkylmercaptoketones, cysteine, cystine, homocysteine, methionine, thiodiglycolic acid, thiodipropionic acid, thioglycerol, selenocysteine, selenomethionine and salts, esters, amides and thioethers thereof; and combinations thereof. More particularly, one or more HCAs can be selected from N-acetylcysteine, N-acetylcysteine butyl ester, N-acetylcysteine dodecyl ester, N-acetylcysteine ethyl ester, N-acetylcysteine methyl ester, N-acetylcysteine octyl ester, N-acetylcysteine propyl ester, N-acetylcysteine stearyl ester, N-acetylcysteine tetradecyl ester, N-acetylcysteine tridecyl ester, N-acetylmethionine, N-acetylmethionine butyl ester, N-acetylmethionine dodecyl ester, N-acetylmethionine ethyl ester, N-acetylmethionine methyl ester, N-acetylmethionine octyl ester, N-acetylmethionine propyl ester, N-acetylmethionine stearyl ester, N-acetylmethionine tetradecyl ester, N-acetylmethionine tridecyl ester, N-acetylselenocysteine, N-acetylselenocysteine butyl ester, N-acetylselenocysteine dodecyl ester, N-acetylselenocysteine ethyl ester, N-acetylselenocysteine methyl ester, N-acetylselenocysteine octyl ester, N-acetylselenocysteine propyl ester, N-acetylselenocysteine stearyl ester, N-acetylselenocysteine tetradecyl ester, N-acetylselenocysteine tridecyl ester, N-acetylselenomethionine, N-acetylselenomethionine butyl ester, N-acetylselenomethionine dodecyl ester, N-acetylselenomethionine ethyl ester, N-acetylselenomethionine methyl ester, N-acetylselenomethionine octyl ester, N-acetylselenomethionine propyl ester, N-acetylselenomethionine stearyl ester, N-acetylselenomethionine tetradecyl ester, N-acetylselenomethionine tridecyl ester, cysteine, cysteine butyl ester, cysteine dodecyl ester, cysteine ethyl ester, cysteine methyl ester, cysteine octyl ester, cysteine propyl ester, cysteine stearyl ester, cysteine tetradecyl ester, cysteine tridecyl ester, cystine, cystine dibutyl ester, cystine di(dodecyl) ester, cystine diethyl ester, cystine dimethyl ester, cystine dioctyl ester, cystine dipropyl ester, cystine distearyl ester, cystine di(tetradecyl) ester, cystine di(tridecyl) ester, N,N-diacetylcystine, N,N-diacetylcystine dibutyl ester, N,N-diacetylcystine diethyl ester, N,N-diacetylcystine di(dodecyl) ester, N,N-diacetylcystine dimethyl ester, N,N-diacetylcystine dioctyl ester, N,N-diacetylcystine dipropyl ester, N,N-diacetylcystine distearyl ester, N,N-diacetylcystine di(tetradecyl) ester, N,N-diacetylcystine di(tridecyl) ester, dibutyl thiodiglycolate, dibutyl thiodipropionate, di(dodecyl) thiodiglycolate, di(dodecyl) thiodipropionate, diethyl thiodiglycolate, diethyl thiodipropionate, dimethyl thiodiglycolate, dimethyl thiodipropionate, dioctyl thiodiglycolate, dioctyl thiodipropionate, dipropyl thiodiglycolate, dipropyl thiodipropionate, distearyl thiodiglycolate, distearyl thiodipropionate, di(tetradecyl) thiodiglycolate, di(tetradecyl) thiodipropionate, homocysteine, homocysteine butyl ester, homocysteine dodecyl ester, homocysteine ethyl ester, homocysteine methyl ester, homocysteine octyl ester, homocysteine propyl ester, homocysteine stearyl ester, homocysteine tetradecyl ester, homocysteine tridecyl ester, methionine, methionine butyl ester, methionine dodecyl ester, methionine ethyl ester, methionine methyl ester, methionine octyl ester, methionine propyl ester, methionine stearyl ester, methionine tetradecyl ester, methionine tridecyl ester, S-methylcysteine, S-methylcysteine butyl ester, S-methylcysteine dodecyl ester, S-methylcysteine ethyl ester, S-methylcysteine methyl ester, S-methylcysteine octyl ester, S-methylcysteine propyl ester, S-methylcysteine stearyl ester, S-methylcysteine tetradecyl ester, S-methylcysteine tridecyl ester, selenocysteine, selenocysteine butyl ester, selenocysteine dodecyl ester, selenocysteine ethyl ester, selenocysteine methyl ester, selenocysteine octyl ester, selenocysteine propyl ester, selenocysteine stearyl ester, selenocysteine tetradecyl ester, selenocysteine tridecyl ester, selenomethionine, selenomethionine butyl ester, selenomethionine dodecyl ester, selenomethionine ethyl ester, selenomethionine methyl ester, selenomethionine octyl ester, selenomethionine propyl ester, selenomethionine stearyl ester, selenomethionine tetradecyl ester, selenomethionine tridecyl ester, thiodiglycolic acid, thiodipropionic acid, thioglycerol, isomers and mixtures of isomers thereof, and salts thereof.

Salts of HCA compounds can be acid addition salts such as the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate and undecanoate salts. In a particular embodiment, the hydrochloride salt of one of the compounds individually mentioned above is present in the composition in an antioxidant effective amount.

Without being bound by theory, it is generally believed that heavier-chalcogen antioxidants such as those exemplified above protect the active compound by being themselves more readily oxidizable and, therefore, being oxidized preferentially over the drug compound. In general, for this mode of operation to provide an acceptable degree of protection for the drug compound, the antioxidant must be present in a substantial amount, for example in a molar ratio to the drug compound of at least about 1:10. In some embodiments, the molar ratio of antioxidant to the drug compound is about 1:10 to about 2:1, for example about 1:5 to about 1.5:1. Best results will sometimes be obtained when the molar ratio is approximately 1:1, i.e., about 8:10 to about 10:8.

An alternative to the HCAs described above can be provided by a different class of sulfur-containing antioxidants, namely inorganic antioxidants of the sulfite, bisulfite, metabisulfite and thiosulfate classes. To complicate matters, these antioxidants are poorly lipid-soluble and must be introduced to a lipid-based carrier or drug-carrier system in aqueous solution. Presence of water promotes sulfoxide formation in ABT-263 solutions, the very effect that is sought to be minimized. To restrict the amount of added water, poorly lipid-soluble antioxidants are typically added at much lower concentrations than those providing molar equivalence to the concentration of ABT-263.

Where a poorly lipid-soluble antioxidant such as a sulfite, bisulfite, metabisulfite or thiosulfate antioxidant is used, it is accompanied in the drug-carrier system by water in an amount not exceeding about 1% by weight, for example about 0.2% to about 0.8% by weight. The amount of such antioxidant that can be introduced in such a small amount of water typically does not exceed about 0.2% by weight, and is for example an amount of about 0.02% to about 0.2%, or about 0.05% to about 0.15%, by weight, of the drug-carrier system.

To minimize the amount of water added to the formulation, it is desirable to provide the antioxidant in the form of a relatively concentrated aqueous stock solution, for example having at least about 10% by weight antioxidant. However, it has been found that where an excessively concentrated stock solution (e.g., about 20% or higher) is used, this can result in undesirable precipitation of solids in the formulation. Suitable concentrations of antioxidant in the stock solution are typically about 10% to about 18%, illustratively about 15%, by weight.

Sodium and potassium salts of sulfites, bisulfites, metabisulfites and thiosulfates are useful antioxidants according to the present embodiment; more particularly sodium and potassium metabisulfites.

To further minimize sulfoxide formation, a chelating agent such as EDTA or a salt thereof (e.g., disodium EDTA or calcium disodium EDTA) is optionally added, for example in an amount of about 0.002% to about 0.02% by weight of the drug-carrier system. EDTA can be added as an aqueous stock solution in the same manner as the antioxidant. The antioxidant and EDTA can, if desired, be added as components of the same stock solution. Chelating agents sequester metal ions that can promote oxidative degradation.

Sulfoxide formation can be further minimized by selecting formulation ingredients having low peroxide value. Peroxide value is a well established property of pharmaceutical excipients and is generally expressed (as herein) in units corresponding to milliequivalents of peroxides per kilogram of excipient (meq/kg). Some excipients inherently have low peroxide value, but others, for example those having unsaturated fatty acid such as oleyl moieties and/or polyoxyethylene chains, can be sources of peroxides. In the case of polysorbate 80, for example, it is preferable to select a source of polysorbate 80 having a peroxide value not greater than about 5, for example not greater than about 2. Suitable sources include Crillet 4HP™ and Super-Refined Tween 80™, both available from Croda.

Without being bound by theory, it is believed that the therapeutic efficacy of ABT-263 is due at least in part to its ability to bind to a Bcl-2 family protein such as Bcl-2, Bcl-$X_L$ or Bcl-w in a way that inhibits the anti-apoptotic action of the protein, for example by occupying the BH3 binding groove of the protein.

As a still further embodiment of the invention, there is provided a method for treating a disease characterized by apoptotic dysfunction and/or overexpression of an anti-apoptotic Bcl-2 family protein, comprising administering to a subject having the disease a therapeutically effective amount of ABT-263 bis-HCl or a pharmaceutical composition comprising ABT-263 bis-HCl and one or more pharmaceutically acceptable excipients.

The subject can be human or non-human (e.g., a farm, zoo, work or companion animal, or a laboratory animal used as a model) but in an important embodiment the subject is a human patient in need of the drug, for example to treat a disease characterized by apoptotic dysfunction and/or overexpression of an anti-apoptotic Bcl-2 family protein. A human subject can be male or female and of any age. The patient is typically an adult, but a method of the invention can be useful to treat a childhood cancer such as leukemia, for example acute lymphocytic leukemia, in a pediatric patient.

The composition is normally administered in an amount providing a therapeutically effective daily dose of the drug. The term "daily dose" herein means the amount of drug administered per day, regardless of the frequency of administration. For example, if the subject receives a unit dose of 150 mg twice daily, the daily dose is 300 mg. Use of the term "daily dose" will be understood not to imply that the specified dosage amount is necessarily administered once daily. However, in a particular embodiment the dosing frequency is once daily (q.d.), and the daily dose and unit dose are in this embodiment the same thing.

What constitutes a therapeutically effective dose depends on the bioavailability of the particular formulation, the subject (including species and body weight of the subject), the disease (e.g., the particular type of cancer) to be treated, the stage and/or severity of the disease, the individual subject's tolerance of the compound, whether the compound is administered in monotherapy or in combination with one or more other drugs, e.g., other chemotherapeutics for treatment of cancer, and other factors. Thus the daily dose can vary within wide margins, for example from about 10 to about 1,000 mg. Greater or lesser daily doses can be appropriate in specific situations. It will be understood that recitation herein of a "therapeutically effective" dose herein does not necessarily require that the drug be therapeutically effective if only a single such dose is administered; typically therapeutic efficacy depends on the composition being administered repeatedly according to a regimen involving appropriate frequency and duration of administration. It is strongly preferred that, while the daily dose selected is sufficient to provide benefit in terms of treating the cancer, it should not be sufficient to provoke an adverse side-effect to an unacceptable or intolerable degree. A suitable therapeutically effective dose can be selected by the physician of ordinary skill without undue experimentation based on the disclosure herein and on art cited herein, taking into account factors such as those mentioned above. The physician may, for example, start a cancer patient on a course of therapy with a relatively low daily dose and titrate the dose upwards over a period of days or weeks, to reduce risk of adverse side-effects.

Illustratively, suitable doses of ABT-263 are generally about 25 to about 1,000 mg/day, more typically about 50 to about 500 mg/day or about 200 to about 400 mg/day, for example about 50, about 100, about 150, about 200, about 250, about 300, about 350, about 400, about 450 or about 500 mg/day, administered at an average dosage interval of about 3 hours to about 7 days, for example about 8 hours to about 3 days, or about 12 hours to about 2 days. In most cases a once-daily (q.d.) administration regimen is suitable.

An "average dosage interval" herein is defined as a span of time, for example one day or one week, divided by the number of unit doses administered over that span of time. For example, where a drug is administered three times a day, around 8 am, around noon and around 6 pm, the average dosage interval is 8 hours (a 24-hour time span divided by 3). If the drug is formulated as a discrete dosage form such as a tablet or capsule, a plurality (e.g., 2 to about 10) of dosage forms administered at one time is considered a unit dose for the purpose of defining the average dosage interval.

A daily dosage amount and dosage interval can, in some embodiments, be selected to maintain a plasma concentration of ABT-263 in a range of about 0.5 to about 10 µg/ml. Thus, during a course of ABT-263 therapy according to such embodiments, the steady-state peak plasma concentration ($C_{max}$) should in general not exceed about 10 µg/ml, and the steady-state trough plasma concentration ($C_{min}$) should in general not fall below about 0.5 µg/ml. It will further be found desirable to select, within the ranges provided above, a daily dosage amount and average dosage interval effective to provide a $C_{max}/C_{min}$ ratio not greater than about 5, for example not greater than about 3, at steady-state. It will be understood that longer dosage intervals will tend to result in greater $C_{max}/C_{min}$ ratios. Illustratively, at steady-state, an ABT-263 $C_{max}$ of about 3 to about 8 µg/ml and $C_{min}$ of about 1 to about 5 µg/ml can be targeted by the present method. Steady-state values of $C_{max}$ and $C_{min}$ can be established in a human PK study, for example conducted according to standard protocols including but not limited to those acceptable to a regulatory agency such as the U.S. Food and Drug Administration (FDA).

As compositions of the present invention are believed to exhibit only a minor food effect, administration according to the present embodiment can be with or without food, i.e., in a non-fasting or fasting condition. It is generally preferred to administer the present compositions to a non-fasting patient.

Compositions of the invention are suitable for use in monotherapy or in combination therapy, for example with other chemotherapeutics or with ionizing radiation. A particular advantage of the present invention is that it permits once-daily oral administration, a regimen which is convenient for the patient who is undergoing treatment with other orally administered drugs on a once-daily regimen. Oral administration is easily accomplished by the patient him/herself or by a caregiver in the patient's home; it is also a convenient route of administration for patients in a hospital or residential care setting.

Combination therapies illustratively include administration of a composition of the present invention comprising ABT-263 bis-HCl concomitantly with one or more of bortezomid, carboplatin, cisplatin, cyclophosphamide, dacarbazine, dexamethasone, docetaxel, doxorubicin, etoposide, fludarabine, hydroxydoxorubicin, irinotecan, paclitaxel, rapamycin, rituximab, vincristine and the like, for example with a polytherapy such as CHOP (cyclophosphamide+hydroxydoxorubicin+vincristine+prednisone), RCVP (rituximab+cyclophosphamide+vincristine+prednisone), R-CHOP (rituximab+CHOP) or DA-EPOCH-R (dose-adjusted etoposide, prednisone, vincristine, cyclophosphamide, doxorubicin and rituximab).

A composition of the invention comprising ABT-263 bis-HCl can be administered in combination therapy with one or more therapeutic agents that include, but are not limited to, angiogenesis inhibitors, antiproliferative agents, other apoptosis promoters (for example, Bcl-xL, Bcl-w and Bfl-1 inhibitors), activators of a death receptor pathway, BiTE (bi-specific T-cell engager) antibodies, dual variable domain binding proteins (DVDs), inhibitors of apoptosis proteins (IAPs), microRNAs, mitogen-activated extracellular signal-regulated kinase inhibitors, multivalent binding proteins, poly-ADP (adenosine diphosphate)-ribose polymerase (PARP) inhibitors, small inhibitory ribonucleic acids (siRNAs), kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDs), antimitotic agents, alkylating agents, antimetabolites, intercalating antibiotics, platinum-containing chemotherapeutic agents, growth factor inhibitors, ionizing radiation, cell cycle inhibitors, enzymes, topoisomerase inhibitors, biologic response modifiers, immunologicals, antibodies, hormonal therapies, retinoids, deltoids, plant alkaloids, proteasome inhibitors, HSP-90 inhibitors, histone deacetylase (HDAC) inhibitors, purine analogs, pyrimidine analogs, MEK inhibitors, CDK inhibitors, ErbB2 receptor inhibitors, mTOR inhibitors as well as other antitumor agents.

Angiogenesis inhibitors include, but are not limited to, EGFR inhibitors, PDGFR inhibitors, VEGFR inhibitors, TIE2 inhibitors, IGF1R inhibitors, matrix metalloproteinase 2 (MMP-2) inhibitors, matrix metalloproteinase 9 (MMP-9) inhibitors and thrombospondin analogs.

Examples of EGFR inhibitors include, but are not limited to, gefitinib, erlotinib, cetuximab, EMD-7200, ABX-EGF, HR3, IgA antibodies, TP-38 (IVAX), EGFR fusion protein, EGF-vaccine, anti-EGFR immunoliposomes and lapatinib.

Examples of PDGFR inhibitors include, but are not limited to, CP-673451 and CP-868596.

Examples of VEGFR inhibitors include, but are not limited to, bevacizumab, sunitinib, sorafenib, CP-547632, axitinib, vandetanib, AEE788, AZD-2171, VEGF trap, vatalanib, pegaptanib, IM862, pazopanib, ABT-869 and angiozyme.

Bcl-2 family protein inhibitors other than ABT-263 or compounds of Formula I herein include, but are not limited to, AT-101 ((−)gossypol), Genasense™ Bcl-2-targeting antisense oligonucleotide (G3139 or oblimersen), IPI-194, IPI-565, ABT-737, GX-070 (obatoclax) and the like.

Activators of a death receptor pathway include, but are not limited to, TRAIL, antibodies or other agents that target death receptors (e.g., DR4 and DR5) such as apomab, conatumumab, ETR2-ST01, GDC0145 (lexatumumab), HGS-1029, LBY-135, PRO-1762 and trastuzumab.

Examples of thrombospondin analogs include, but are not limited to, TSP-1, ABT-510, ABT-567 and ABT-898.

Examples of aurora kinase inhibitors include, but are not limited to, VX-680, AZD-1152 and MLN-8054.

An example of a polo-like kinase inhibitor includes, but is not limited to, BI-2536.

Examples of bcr-abl kinase inhibitors include, but are not limited to, imatinib and dasatinib.

Examples of platinum-containing agents include, but are not limited to, cisplatin, carboplatin, eptaplatin, lobaplatin, nedaplatin, oxaliplatin and satraplatin.

Examples of mTOR inhibitors include, but are not limited to, CCI-779, rapamycin, temsirolimus, everolimus, RAD001 and AP-23573.

Examples of HSP-90 inhibitors include, but are not limited to, geldanamycin, radicicol, 17-AAG, KOS-953, 17-DMAG, CNF-101, CNF-1010, 17-AAG-nab, NCS-683664, efungumab, CNF-2024, PU3, PU24FCl, VER-49009, IPI-504, SNX-2112 and STA-9090.

Examples of HDAC inhibitors include, but are not limited to, suberoylanilide hydroxamic acid (SAHA), MS-275, valproic acid, TSA, LAQ-824, trapoxin and depsipeptide.

Examples of MEK inhibitors include, but are not limited to, PD-325901, ARRY-142886, ARRY-438162 and PD-98059.

Examples of CDK inhibitors include, but are not limited to, flavopyridol, MCS-5A, CVT-2584, seliciclib ZK-304709, PHA-690509, BMI-1040, GPC-286199, BMS-387032, PD-332991 and AZD-5438.

Examples of COX-2 inhibitors include, but are not limited to, celecoxib, parecoxib, deracoxib, ABT-963, etoricoxib, lumiracoxib, BMS-347070, RS 57067, NS-398, valdecoxib, rofecoxib, SD-8381, 4-methyl-2-(3,4-dimethylphenyl)-1-(4-sulfamoylphenyl)-1H-pyrrole, T-614, JTE-522, S-2474, SVT-2016, CT-3 and SC-58125.

Examples of NSAIDs include, but are not limited to, salsalate, diflunisal, ibuprofen, ketoprofen, nabumetone, piroxicam, naproxen, diclofenac, indomethacin, sulindac, tolmetin, etodolac, ketorolac and oxaprozin.

Examples of ErbB2 receptor inhibitors include, but are not limited to, CP-724714, canertinib, trastuzumab, petuzumab, TAK-165, ionafamib, GW-282974, EKB-569, PI-166, dHER2, APC-8024, anti-HER/2neu bispecific antibody B7.her2IgG3 and HER2 trifunctional bispecific antibodies mAB AR-209 and mAB 2B-1.

Examples of alkylating agents include, but are not limited to, nitrogen mustard N-oxide, cyclophosphamide, ifosfamide, trofosfamide, chlorambucil, melphalan, busulfan, mitobronitol, carboquone, thiotepa, ranimustine, nimustine, Cloretazine™ (laromustine), AMD-473, altretamine, AP-5280, apaziquone, brostallicin, bendamustine, carmustine, estramustine, fotemustine, glufosfamide, KW-2170, mafosfamide, mitolactol, lomustine, treosulfan, dacarbazine and temozolomide.

Examples of antimetabolites include, but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, pemetrexed, gemcitabine, fludarabine, 5-azacitidine, capecitabine, cladribine, clofarabine, decitabine, eflornithine, ethenylcytidine, cytosine arabinoside, hydroxyurea, TS-1, melphalan, nelarabine, nolatrexed, disodium pemetrexed, pentostatin, pelitrexol, raltitrexed, triapine, trimetrexate, vidarabine, mycophenolic acid, ocfosfate, pentostatin, tiazofurin, ribavirin, EICAR, hydroxyurea and deferoxamine.

Examples of antibiotics include, but are not limited to, intercalating antibiotics, aclarubicin, actinomycin D, amrubicin, annamycin, adriamycin, bleomycin, daunorubicin, doxorubicin (including liposomal doxorubicin), elsamitrucin, epirubicin, glarubicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, aclarubicin, amonafide, belotecan, camptothecin, 10-hydroxycamptothecin, 9-amino-camptothecin, amsacrine, dexrazoxane, diflomotecan, irinotecan HCl, edotecarin, epirubicin, etoposide, exatecan, becatecarin, gimatecan, lurtotecan, orathecin, BN-80915, mitoxantrone, pirarbucin, pixantrone, rubitecan, sobuzoxane, SN-38, tafluposide and topotecan.

Examples of antibodies include, but are not limited to, rituximab, cetuximab, bevacizumab, trastuzumab, CD40-specific antibodies and IGF1R-specific antibodies, chTNT-1/B, denosumab, edrecolomab, WX G250, zanolimumab, lintuzumab and ticilimumab.

Examples of hormonal therapies include, but are not limited to, sevelamer carbonate, rilostane, luteinizing hormone releasing hormone, modrastane, exemestane, leuprolide acetate, buserelin, cetrorelix, deslorelin, histrelin, anastrozole, fosrelin, goserelin, degarelix, doxercalciferol, fadrozole, formestane, tamoxifen, arzoxifene, bicalutamide, abarelix, triptorelin, finasteride, fulvestrant, toremifene, raloxifene, trilostane, lasofoxifene, letrozole, flutamide, megesterol, mifepristone, nilutamide, dexamethasone, prednisone and other glucocorticoids.

Examples of retinoids or deltoids include, but are not limited to, seocalcitol, lexacalcitol, fenretinide, aliretinoin, tretinoin, bexarotene and LGD-1550.

Examples of plant alkaloids include, but are not limited to, vincristine, vinblastine, vindesine and vinorelbine.

Examples of proteasome inhibitors include, but are not limited to, bortezomib, MG-132, NPI-0052 and PR-171.

Examples of immunologicals include, but are not limited to, interferons and numerous other immune-enhancing agents. Interferons include interferon alpha, interferon alpha-2a, interferon alpha-2b, interferon beta, interferon gamma-1a, interferon gamma-1b, interferon gamma-n1 and combinations thereof. Other agents include filgrastim, lentinan, sizofilan, BCG live, ubenimex, WF-10 (tetrachlorodecaoxide or TCDO), aldesleukin, alemtuzumab, BAM-002, dacarbazine, daclizumab, denileukin, gemtuzumab ozogamicin, ibritumomab, imiquimod, lenograstim, melanoma vaccine, molgramostim, sargaramostim, tasonermin, tecleukin, thymalasin, tositumomab, Virulizin™ immunotherapeutic of Lorus Pharmaceuticals, Z-100 (specific substance of Maruyama or SSM), Zevalin™ (90Y-ibritumomab tiuxetan), epratuzumab, mitumomab, oregovomab, pemtumomab, Provenge™ (sipuleucel-T), teceleukin, Therocys™ (Bacillus Calmette-Guerin), cytotoxic lymphocyte antigen 4 (CTLA4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include, but are not limited to, krestin, lentinan, sizofuran, picibanil, PF-3512676 and ubenimex.

Examples of pyrimidine analogs include, but are not limited to, 5-fluorouracil, floxuridine, doxifluridine, raltitrexed, cytarabine, cytosine arabinoside, fludarabine, triacetyluridine, troxacitabine and gemcitabine.

Examples of purine analogs include, but are not limited to, mercaptopurine and thioguanine.

Examples of antimitotic agents include, but are not limited to, N-(2-((4-hydroxyphenyl)amino)pyridin-3-yl)-4-methoxybenzenesulfonamide, paclitaxel, docetaxel, larotaxel, epothilone D, PNU-100940, batabulin, ixabepilone, patupilone, XRP-9881, vinflunine and ZK-EPO (synthetic epothilone).

Examples of radiotherapy include, but are not limited to, external beam radiotherapy (XBRT), teletherapy, brachytherapy, sealed-source radiotherapy and unsealed-source radiotherapy.

BiTE antibodies are bi-specific antibodies that direct T-cells to attack cancer cells by simultaneously binding the two cells. The T-cell then attacks the target cancer cell. Examples of BiTE antibodies include, but are not limited to, adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (Sutton et al. (1997) *J. Immunol.* 158:5783-5790).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-$OCH_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263 (Tse et al. (2008) *Cancer Res.* 68:3421-3428 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy-chain DVD polypeptides and two light-chain DVD polypeptides are referred to as DVD Ig's. Each half of a DVD Ig comprises a heavy-chain DVD polypeptide, a light-chain DVD polypeptide, and two antigen binding sites. Each binding site comprises a heavy-chain variable domain and a light-chain variable domain with a total of 6 CDRs involved in antigen binding per antigen binding site.

PARP inhibitors include, but are not limited to, ABT-888, olaparib, KU-59436, AZD-2281, AG-014699, BSI-201, BGP-15, INO-1001, ONO-2231 and the like.

Additionally or alternatively, a composition of the present invention can be administered in combination therapy with one or more antitumor agents selected from ABT-100, N-acetylcolchinol-O-phosphate, acitretin, AE-941, aglycon protopanaxadiol, arglabin, arsenic trioxide, AS04 adjuvant-adsorbed HPV vaccine, L-asparaginase, atamestane, atrasentan, AVE-8062, bosentan, canfosfamide, Canvaxin™, catumaxomab, CeaVac™, celmoleukin, combrestatin A4P, contusugene ladenovec, Cotara™, cyproterone, deoxycoformycin, dexrazoxane, N,N-diethyl-2-(4-(phenylmethyl)phenoxy)ethanamine, 5,6-dimethylxanthenone-4-acetic acid, docosahexaenoic acid/paclitaxel, discodermolide, efaproxiral, enzastaurin, epothilone B, ethynyluracil, exisulind, falimarev, Gastrimmune™, GMK vaccine, GVAX™, halofuginone, histamine, hydroxycarbamide, ibandronic acid, ibritumomab tiuxetan, IL-13-PE38, inalimarev, interleukin 4, KSB-311, lanreotide, lenalidomide, lonafarnib, lovastatin, 5,10-methylenetetrahydrofolate, mifamurtide, miltefosine, motexafin, oblimersen, OncoVAX™, Osidem™, paclitaxel albumin-stabilized nanoparticle, paclitaxel poliglumex, pamidronate, panitumumab, peginterferon alfa, pegaspargase, phenoxodiol, poly(I)-poly(C12U), procarbazine, ranpirnase, rebimastat, recombinant quadrivalent HPV vaccine, squalamine, staurosporine, STn-KLH vaccine, T4 endonuclease V, tazarotene, 6,6',7,12-tetramethoxy-2,2'-dimethyl-1β-berbaman, thalidomide, TNFerade™, $^{131}$I-tositumomab, trabectedin, triazone, tumor necrosis factor, Ukrain™, vaccinia-MUC-1 vaccine, L-valine-L-boroproline, Vitaxin™, vitespen, zoledronic acid and zorubicin.

In one embodiment, a composition of the invention comprising ABT-263 bis-HCl is administered in a therapeutically effective amount to a subject in need thereof to treat a disease during which is overexpressed one or more of antiapoptotic Bcl-2 protein, antiapoptotic Bcl-$X_L$ protein and antiapoptotic Bcl-w protein.

In another embodiment, a composition of the invention comprising ABT-263 bis-HCl is administered in a therapeutically effective amount to a subject in need thereof to treat a disease of abnormal cell growth and/or dysregulated apoptosis.

Examples of such diseases include, but are not limited to, cancer, mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof.

In a more particular embodiment, a composition of the invention comprising ABT-263 bis-HCl is administered in a therapeutically effective amount to a subject in need thereof to treat bladder cancer, brain cancer, breast cancer, bone marrow cancer, cervical cancer, chronic lymphocytic leukemia, acute lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small-cell lung cancer, prostate cancer, small-cell lung cancer or spleen cancer.

According to any of these embodiments, the composition is administered in monotherapy or in combination therapy with one or more additional therapeutic agents.

For example, a method for treating mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, acute lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof in a subject comprises administering to the subject therapeutically effective amounts of (a) a composition of the invention comprising ABT-263 bis-HCl, and (b) one or more of etoposide, vincristine, CHOP, rituximab, rapamycin, R-CHOP, RCVP, DA-EPOCH-R or bortezomib.

In particular embodiments, a composition of the invention comprising ABT-263 bis-HCl is administered in a therapeutically effective amount to a subject in need thereof in monotherapy or in combination therapy with etoposide, vincristine, CHOP, rituximab, rapamycin, R-CHOP, RCVP, DA-EPOCH-R or bortezomib in a therapeutically effective amount, for treatment of a lymphoid malignancy such as B-cell lymphoma or non-Hodgkin's lymphoma.

In other particular embodiments, a composition of the invention comprising ABT-263 bis-HCl is administered in a therapeutically effective amount to a subject in need thereof in monotherapy or in combination therapy with etoposide, vincristine, CHOP, rituximab, rapamycin, R-CHOP, RCVP, DA-EPOCH-R or bortezomib in a therapeutically effective amount, for treatment of chronic lymphocytic leukemia or acute lymphocytic leukemia.

The present invention also provides a method for maintaining in bloodstream of a human cancer patient a therapeutically effective plasma concentration of ABT-263 and/or one or more metabolites thereof, comprising administering to the subject a pharmaceutical composition as described herein, in a dosage amount equivalent to about 50 to about 500 mg ABT-263 per day, at an average dosage interval of about 3 hours to about 7 days.

What constitutes a therapeutically effective plasma concentration depends inter alia on the particular cancer present in the patient, the stage, severity and aggressiveness of the cancer, and the outcome sought (e.g., stabilization, reduction in tumor growth, tumor shrinkage, reduced risk of metastasis, etc.). It is strongly preferred that, while the plasma concentration is sufficient to provide benefit in terms of treating the cancer, it should not be sufficient to provoke an adverse side-effect to an unacceptable or intolerable degree.

For treatment of cancer in general and of a lymphoid malignancy such as non-Hodgkin's lymphoma in particular, the plasma concentration of ABT-263 should in most cases be maintained in a range of about 0.5 to about 10 μg/ml. Thus, during a course of ABT-263 therapy, the steady-state $C_{max}$ should in general not exceed about 10 μg/ml, and the steady-state $C_{min}$ should in general not fall below about 0.5 μg/ml. It will further be found desirable to select, within the ranges provided above, a daily dosage amount and average dosage interval effective to provide a $C_{max}/C_{min}$ ratio not greater than about 5, for example not greater than about 3, at steady-state. It will be understood that longer dosage intervals will tend to result in greater $C_{max}/C_{min}$ ratios. Illustratively, at steady-state, an ABT-263 $C_{max}$ of about 3 to about 8 μg/ml and $C_{min}$ of about 1 to about 5 μg/ml can be targeted by the present method.

A daily dosage amount effective to maintain a therapeutically effective ABT-263 plasma level is, according to the present embodiment, about 50 to about 500 mg. In most cases a suitable daily dosage amount is about 200 to about 400 mg. Illustratively, the daily dosage amount can be for example about 50, about 100, about 150, about 200, about 250, about 300, about 350, about 400, about 450 or about 500 mg.

An average dosage interval effective to maintain a therapeutically effective ABT-263 plasma level is, according to the present embodiment, about 3 hours to about 7 days. In most cases a suitable average dosage interval is about 8 hours to about 3 days, or about 12 hours to about 2 days. A once-daily (q.d.) administration regimen is often suitable.

As in other embodiments, administration according to the present embodiment can be with or without food, i.e., in a non-fasting or fasting condition. It is generally preferred to administer the present compositions to a non-fasting patient.

Further information of relevance to the present invention is available in a recently published article by Tse et al. (2008) *Cancer Res.* 68:3421-3428 and supplementary data thereto available at Cancer Research Online (cancerres.aacrjournals.org/). This article and its supplementary data are incorporated in their entirety herein by reference.

What is claimed is:

1. The compound N-(4-(4-((2-(4-chlorophenyl)-5,5-dimethyl-1-cyclohex-1-en-1-yl)methyl)piperazin-1-yl)benzoyl)-4-(((1R1-3-(morpholin-4-yl)-1-((phenylsulfanyl)methyl)propyl)amino-3-((trifluoromethyl)sulfonyl) benzenesulfonamide bis-hydrochloride (ABT-263 bis-HCl) in crystalline polymorph Form I thereof, characterized at least by a powder X-ray diffraction peak at any one or more of the following positions: 6.8, 7.2, 8.5, 18.5 and 18.7° 2θ, ±0.2° 2θ.

2. The crystalline polymorph of claim 1, characterized at least by a powder X-ray diffraction peak at each of said positions.

3. The crystalline polymorph of claim 1, characterized by a powder X-ray diffraction pattern substantially as indicated in the following table:

| Peak Position (°2θ) | Relative Intensity |
| --- | --- |
| 6.8 | 59.0 |
| 7.2 | 75.9 |
| 8.5 | 14.3 |
| 9.3 | 4.3 |
| 11.2 | 6.5 |
| 13.8 | 15.8 |
| 14.0 | 17.7 |
| 14.9 | 9.5 |
| 16.7 | 17.5 |
| 17.5 | 15.7 |
| 18.2 | 52.2 |
| 18.5 | 100.0 |
| 18.7 | 95.4. |

4. The compound of N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino-3-((trifluoromethyl)sulfonyl) benzenesulfonamide bis-hydrochloride (ABT-263 bis-HCl) in crystalline polymorph Form II thereof, characterized at least by a powder X-ray diffraction peak at 3.7 or 7.4° 2θ, ±0.2° 2θ.

5. The crystalline polymorph of claim 4, characterized at least by a powder X-ray diffraction peak at both 3.7 and 7.4° 2θ, ±0.2° 2θ.

6. The crystalline polymorph of claim 4, characterized by a powder X-ray diffraction pattern substantially as indicated in the following table:

| Peak position (°2θ) | Relative intensity |
| --- | --- |
| 3.7 | 6.0 |
| 7.4 | 100.0 |
| 12.1 | 5.3 |
| 15.6 | 8.6 |
| 16.1 | 16.2 |
| 16.6 | 21.6 |
| 18.3 | 70.2 |
| 19.0 | 13.4. |

7. A crystalline solvate comprising N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino-3-((trifluoromethyl)sulfonyl) benzenesulfonamide bis-hydrochloride (ABT-263 bis-HCl) solvated with an organic solvent.

8. The solvate of claim 7, wherein the organic solvent is selected from the group consisting of ethanol, 1-propanol, 2-propanol, 2-butanol, t-butanol, nitromethane, acetonitrile, propionitrile, ethyl formate, methyl acetate, ethyl acetate, isopropyl acetate, acetone, methyl ethyl ketone, methyl isopropyl ketone, 1,4-dioxane, benzene, toluene and butyl ether.

9. A pharmaceutical composition comprising crystalline polymorph Form I of ABT-263 bis-HCl and one or more pharmaceutically acceptable excipients.

10. A pharmaceutical composition comprising crystalline polymorph Form II of ABT-263 bis-HCl and one or more pharmaceutically acceptable excipients.

* * * * *